United States Patent
Li et al.

(10) Patent No.: US 8,055,345 B2
(45) Date of Patent: **\*Nov. 8, 2011**

(54) SELF-REFERENCING COMMUNICATION IN IMPLANTABLE DEVICES

(75) Inventors: Haifeng Li, Mountain View, CA (US); Mark Zdeblick, Portola Valley, CA (US); Lawrence Arne, Redwood City, CA (US); Yafei Bi, Fremont, CA (US); Nilay Jani, Palo Alto, CA (US); Jonathan Withrington, San Francisco, CA (US)

(73) Assignee: Proteus Biomedical, Inc., Redwood City, CA (US)

( * ) Notice: Subject to any disclaimer, the term of this patent is extended or adjusted under 35 U.S.C. 154(b) by 514 days.

This patent is subject to a terminal disclaimer.

(21) Appl. No.: 12/202,150

(22) Filed: Aug. 29, 2008

(65) Prior Publication Data

US 2009/0062880 A1    Mar. 5, 2009

Related U.S. Application Data

(60) Provisional application No. 60/969,504, filed on Aug. 31, 2007, provisional application No. 60/972,172, filed on Sep. 13, 2007, provisional application No. 60/981,429, filed on Oct. 19, 2007, provisional application No. 61/053,395, filed on May 15, 2008.

(51) Int. Cl.
   *A61N 1/00* (2006.01)

(52) U.S. Cl. ........................................ 607/32

(58) Field of Classification Search ..................... 607/32
   See application file for complete search history.

(56) References Cited

U.S. PATENT DOCUMENTS

| | | | |
|---|---|---|---|
| 5,870,046 A | 2/1999 | Scott et al. | |
| 7,260,431 B2 * | 8/2007 | Libbus et al. | 607/4 |
| 2004/0193021 A1 | 9/2004 | Zdeblick et al. | |

FOREIGN PATENT DOCUMENTS

| | | |
|---|---|---|
| WO | WO2004/062221 | 7/2004 |
| WO | WO2006029090 A2 | 3/2006 |
| WO | WO2006069322 A2 | 6/2006 |
| WO | WO2006069323 A1 | 6/2006 |
| WO | WO2007/075974 | 7/2007 |
| WO | WO2007120884 A2 | 10/2007 |
| WO | WO2007149546 A2 | 12/2007 |

\* cited by examiner

*Primary Examiner* — George Manuel
(74) *Attorney, Agent, or Firm* — Bozicevic, Field & Francis LLP; Bret E. Field

(57) ABSTRACT

Various aspects of the present invention enable robust, reliable control functionality for effectors present on intraluminal, e.g., vascular leads, as well as other types of implantable devices. Aspects of the invention include implantable integrated circuits that have self-referencing and self-clocking signal encoding, and are capable of bidirectional communication. Also provided by the invention are effector assemblies that include the integrated circuits, as well as implantable medical devices, e.g., pulse generators that include the same, as well as systems and kits thereof and methods of using the same, e.g., in pacing applications, including cardiac resynchronization therapy (CRT) applications.

22 Claims, 24 Drawing Sheets

SELF-REFERENCING COMMUNICATION IN IMPLANTABLE DEVICES

CROSS-REFERENCE TO RELATED APPLICATIONS

Pursuant to 35 U.S.C. §119 (e), this application claims priority to U.S. Provisional Application Ser. No. 60/969,504 filed Aug. 31, 2007; U.S. Provisional Application Ser. No. 60/972,172 filed Sep. 13, 2007; U.S. Provisional Application Ser. No. 60/981,429 filed Oct. 19, 2007 and U.S. Provisional Application Ser. No. 61/053,395 filed May 15, 2008; the disclosures of which priority applications are herein incorporated by reference.

INTRODUCTION

The history of biomedical implantable devices traces back to its beginning in the late 1950s. Since the first development of the implantable cardiac pacemaker over forty years ago, the field of bioengineering has provided many different implantable biomedical devices to the medical profession for the treatment of various conditions. Today, implantable cardioverter/defibrillators, drug delivery systems, neurological stimulators, bone growth stimulators, and many other implantable devices significantly facilitate the treatment of a variety of diseases.

For any type of implantable devices, to be able to precisely control the behavior and to accurately monitor the state of these devices is critically important for effective treatment of the illness. For instance, in cardiac resynchronization therapy (CRT), a pacing lead is often inserted into a patient's heart. The location and timing of the pacing signals applied to the heart tissue can drastically affect the effectiveness of the resynchronization therapy. Ideally, a physician can use an implantable device to monitor the response of the tissue and the state of the implantable device to evaluate the efficacy of the treatment.

The development of biomedical implantable devices reflects, in many ways, the development of electronic technology, particularly the progress in the areas of microelectronics, circuit design, sensing technology, micro electromechanical systems (MEMS), signal processing, and other related fields. However, the latest electronic technologies are often not incorporated in the implantable devices, due to a lack of large-scale collaborative efforts among electrical engineering, bioengineering, and medical science. For example, until recently, a large number of cardiac resynchronization therapists still relied on semi-empirical methods to adjust the pacing lead and pacing signals.

At present, there are only limited applications of automatically controlled implantable devices such as pace makers and neurological stimulators. Moreover, automatic operation of the existing implantable devices often requires bulky external control systems and power sources. Such operation can be difficult to administer and often impossible to manage outside the clinic.

SUMMARY

Aspects of the invention include a communication system between two or more electronic devices that are configured to be implanted in a living subject, such as a human. Communication systems of embodiments of the invention, e.g., as described in greater detail below, are self-referencing, which makes them relatively insensitive to manufacturing variations of the integrated circuits and components thereof. In one embodiment of the communication system, a communication link is established between a central pacing "can" and distributed electronics, e.g., integrated circuits (ICs), on a carrier, e.g., a pacing lead. The communication protocol of this embodiment is implemented without use of a crystal oscillator on the lead ICs. In one embodiment, the protocol makes use of a multi-phase, such as a four-phase, symbol that allows comparisons of the duration of each phase to the other phases of the multi-phase signal to represent information transmitted from the central communication hub to the distributed communication nodes. It also allows information to be sent from the distributed nodes to the central hub by use of a differential amount of current drain during various phases of the symbol. In both cases, an aspect of the invention is that the voltage levels which determine the status of a bit of information are determined using a differential method that is "self-referencing." In this differential or self-referencing method, a first voltage is generated from the transmitted signal during one phase of a transmitted signal. A second voltage is then generated during a second phase of a symbol. The two voltages are proportional to the duration of each phase. The first and second voltages are then compared to each other to determine which is greater. More voltages, e.g., a third and fourth voltage, are also generated during a third and fourth phase and those two voltages are compared. Based upon the relationship between the phases, a multi-value symbol, e.g., 4-value symbol, is derived. In one embodiment of a 4-value symbol, one value is reserved to indicate packet/instruction start and the remaining 3 values describe data values. A packet/instruction is constructed with a start symbol followed by any number of data symbols. In a more complex implementation, the packet/instruction is constructed with start flagged by a unique sequence of symbols followed by any number of symbols with all 4 values encoding data. Another aspect of this invention is that a return information path is provided, where this return information path may be based on a differential or self-referencing protocol, analogous to that described above. In addition, if the current sources or storage capacitors integrated on the substrate, e.g., piece of silicon, vary from ideal during manufacturing, the self-referencing technique of the invention cancels out most of those variations, allowing for more robust transmission of information.

In various aspects, an implantable integrated circuit can include: a first capacitor configured to be charged when a first phase control signal is asserted, where the first phase control signal is related to a first predetermined phase of an encoded signal; a second capacitor configured to be charged when a second phase control signal is asserted, where the second phase control signal is related to a second predetermined phase of the encoded signal; and a comparator coupled to the first and second capacitors, and the comparator can provide a first comparison result that indicates which of the first and second predetermined phases has a longer duration.

In various aspects, a method for clock and data recovery in an implantable device can include: recovering a first clock from first and second high phases of an encoded signal, and a second clock from first and second low phases of the encoded signal; deriving first, second, third, and fourth phase control signals from the first and second recovered clocks; comparing pulse durations of the first and second phase control signal to generate a first comparison result, and comparing pulse durations of the third and fourth phase control signals to generate a second comparison result; and determining one of four symbols corresponding to the encoded signal using the first and second comparison results.

In various aspects, an implantable controller can include an interface configured to communicate to an implantable satellite device, where the interface can include: a ground terminal; and a signal terminal configured to transmit an encoded signal to the implantable satellite device, where the encoded signal can include first and second high phases and first and second low phases.

In various aspects, an implantable system can include: a controller having an amplifier configured to amplify a voltage difference across a variable resistor, the variable resistor being coupled to a first supply voltage and a first lead line, the controller being coupled to the first and a second lead line; and a plurality of implantable integrated circuits coupled to the first and second lead lines, where a selected one of the implantable integrated circuits is configured to reduce an impedance across the first and second lead lines to change the voltage difference for communication of an electrode configuration to be controller.

In various aspects, a method for communicating an electrode configuration of an implantable device can include: receiving a command from a controller; receiving an address from the controller, where the address corresponds to one of a plurality of implantable devices coupled to the controller; and sending a bit string to the controller in response to the command when the address matches a predetermined address of the implantable device, and where the bit string is configured to convey the electrode configuration.

In various aspects, an implantable controller can include an interface configured to communicate with an implantable satellite device, where the interface can include: a ground terminal; and a signal terminal configured to transmit a series of encoded signals to the implantable satellite device, and to receive an electrode configuration of the implantable satellite device in response to the series of encoded signals.

DETAILED DESCRIPTION

Figure 1:
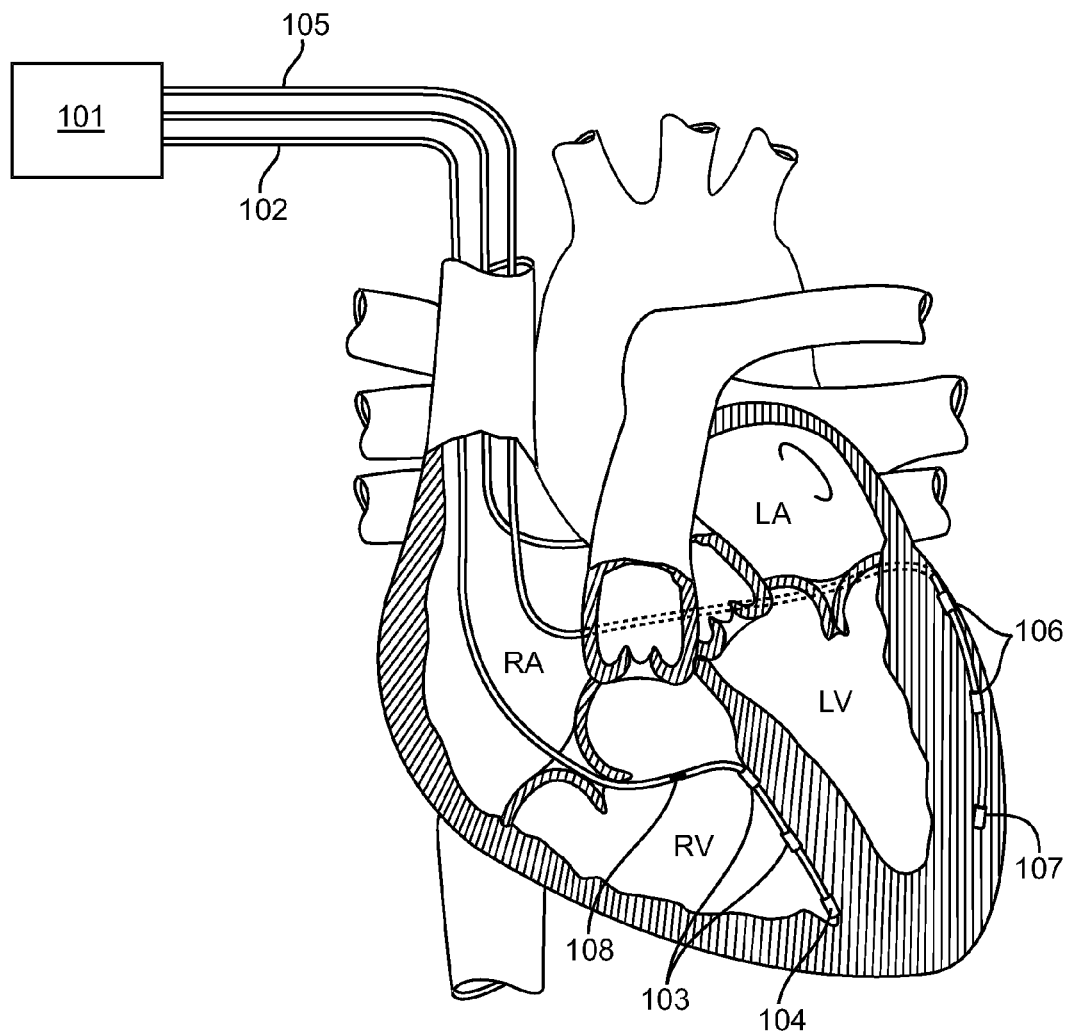
FIG. 1 illustrates the locations of a number of pacing satellites incorporated in multi-electrode pacing leads, in accordance with various aspects of the present invention.

As summarized above, various aspects can enable bidirectional communication suitable for implantable devices requiring a minimized interface. Such advantages provided by various aspects of the present invention enable a variety of different enhanced implantable technologies, such as enhanced implantable pulse generators, e.g., cardiac pacing devices.

Various aspects may include encoded symbols over a single wire transmission. Also provided by the invention are effector assemblies that include the integrated circuits, as well as implantable medical devices, e.g., pulse generators that include the same, as well as systems and kits thereof and methods of using the same, e.g., in pacing applications, including cardiac resynchronization therapy (CRT) applications.

In further describing various aspects of the invention, integrated circuits will be reviewed first in greater detail, both generally and in terms of the figures, followed by a discussion of implantable medical devices that may include the subject circuits and systems thereof, as well as a review of various kits thereof.

Integrated Circuits

Various aspects may provide implantable integrated circuits as described herein. By implantable is meant that the circuits are configured to maintain functionality when present in a physiological environment, including a high salt, high humidity environment found inside of a body, for 2 or more days, such as about 1 week or longer, about 4 weeks or longer, about 6 months or longer, about 1 year or longer, e.g., about 5 years or longer. In various aspects, the implantable circuits are configured to maintain functionality when implanted at a physiological site for a period ranging from about 1 to about 80 years or longer, such as from about 5 to about 70 years or longer, and including for a period ranging from about 10 to about 50 years or longer.

The implantable integrated circuits include a number of distinct functional blocks, i.e., modules, where the functional blocks are all present in a single integrated circuit on an intraluminal-sized support. By single integrated circuit is meant a single circuit structure that includes all of the different functional blocks. As such, the integrated circuit is a monolithic integrated circuit (also known as IC, microcircuit, microchip, silicon chip, computer chip or chip) that is a miniaturized electronic circuit (which may include semiconductor devices, as well as passive components) that has been manufactured in the surface of a thin substrate of semiconductor material. The integrated circuits of various aspects of the present invention are distinct from hybrid integrated circuits, which are miniaturized electronic circuits constructed of individual semiconductor devices, as well as passive components, bonded to a substrate or circuit board.

The support with which the circuit is associated, e.g., by being present on surface of the support or integrated, at least partially, inside of the support, may be any convenient support, and may be rigid or flexible as desired. As the support is intraluminal sized, its dimensions are such that it can be positioned inside of a physiological lumen, e.g., inside of a vessel, such as a cardiac vessel, e.g., a vein or artery. In various aspects, the intraluminal sized integrated circuits have a size (e.g., in terms of surface area of largest surface) of between about 0.05 $mm^2$ and about 5 $mm^2$, such as between about 1.125 $mm^2$ and about 2.5 $mm^2$, and including about 1.5 $mm^2$. The supports of the integrated circuits can have a variety of different shapes, such as square, rectangle, oval, and hexagon, irregular, etc.

As indicated above, the integrated circuits of the invention may include a number of functional blocks which provide for the requisite functionality of the circuit for its intended use, where the functional blocks are all part of a single integrated circuit. In various aspects, the circuits include at least the following functional blocks: a power extraction functional block; an energy storage functional block; a communication functional block; and a device configuration functional block.

The power extraction functional block is a circuitry functional block or module that is configured to extract or obtain power from a power source to which the circuit is coupled. In the broadest sense, the power extraction functional block may be a block that is configured to receive power from an electrically coupled source, e.g., wire, or remotely, e.g., power that is wirelessly transmitted to the circuit from a remote location, where that remote location may be an in vivo or ex vivo location, but is one that is not physically connected to the device by a conductive element, such as a wire. In various aspects, the power extraction functional block is one that is configured to be coupled to at least one wire that is, in turn, coupled to a power source, such as a battery, where the functional block extracts power from the wire to power the circuit.

Another functional block or module present that is part of the integrated circuit is an energy storage functional block. The energy storage functional block is one that is capable of storing energy in the circuit, e.g., in a capacitor fashion, such as the energy extracted by the power extraction block. The energy storage functional block has, in various aspects, an energy storage capacity of about 200 pF or more, such as about 500 pF or more, including about 800 pF or more, and in various aspects the storage capacity of the block is about 5000 pF or less, such as about 2000 pF or less, including about 1000 pF or less. As such, the storage capacity of the functional block may, in various aspects have a total capacity ranging from about 200 to about 5000 pF, such as from about 500 to about 2500 pF, including from about 750 to about 2000 pF. This functional block may be made up of a single discreet circuit element or multiple circuit elements, e.g., two or more, three or more, etc., elements each having a capacity ranging from about 60 to about 220 pF, etc.

The circuits of various aspects further include a communication functional block. This block provides for sending and receiving of data, e.g., in the form of signals, from a location remote to the integrated circuit, be that location in vivo or ex vivo, where the location may be physically connected to the circuit or not. In various aspects, this block is configured to receive command signals from a control unit that is connected to the circuit via at least one wire and/or transmit sensed data signals from the circuit to a control unit over at least one wire, where the control unit is remote from the circuit and physically connected to the circuit by the at least one wire. In various aspects, the communication functional block employs an alternating current at a frequency above about 15 kHz, where the operating frequency of the communication functional block may be about 100 kHz or more, such as about 500 kHz or more, including about 1 MHz or more.

The circuit further includes a device configuration functional block. This block is able to employ configuration commands, e.g., as received from a remote device via the communication block, and configure one or more effectors of the device, e.g., electrodes, according to the received configuration command. In various aspects, the device configuration functional block is configured such that the device configuration provided by the functional block of the integrated circuit is functional without power being applied to said integrated circuit. In various aspects, the device configuration block includes a switching block between supply terminals and one or more effectors. The switching block may include switching elements each made up of two transistors between each effector and supply terminal.

In various aspects, in a given device or system, such as the devices and systems described below, substantially all, if not all of the functions of power extraction, energy storage, communication and device configuration employed by the integrated circuit during use are provided by the single integrated circuit. In yet other aspects, the device or system in which the circuit is present may provide some of the above functionalities. However, even in such aspects, the circuits may still include the above summarized functional blocks.

In various aspects, the integrated circuits are configured to be employed in therapeutic tissue electrical stimulation applications, such as cardiac applications and neurological applications. Cardiac applications of interest include, but are not limited to, cardiac function monitoring applications and/or therapeutic electrical energy delivery applications, e.g., pacing applications. Neurological applications of interest include application where neurological tissues, e.g., central nervous system tissue, peripheral nervous system tissue, is electrically monitored and/or stimulated, e.g., for pain management, etc. As such, the circuits may include a functional block that enables stimulation of tissue via an effector, e.g., electrode, that is coupled to the circuit. The circuits may include a functional block that enables low voltage transmission from tissue, e.g., that is contacting an effector coupled to the circuit, to the integrated circuit. In various aspects, the integrated circuit may provide a substantially charge-balanced transmission of a stimulation pulse to tissue, e.g., that is contacting an effector which is coupled to the circuit. Also of interest is use of the invention in non-stimulation applications, such as applications where one or more types of effectors, such as sensors, are controlled, e.g., such as the effectors described above.

Where desired, the integrated circuit may include one or more integrated corrosion protection films, e.g., which serve as primary protection of the circuit and functional blocks thereof from the implanted environment and impart the implantable functionality to the circuit, e.g., as described above. In various aspects, the integrated corrosion protection films are planar deposited corrosion protection films. In various aspects, the protection films, i.e., layers, are those described in U.S. Provisional Application Ser. No. 60/791,244 titled "Void-Free Implantable Hermetically Sealed Structures" and filed Apr. 12, 2006; the disclosure of which is herein incorporated by reference.

These aforementioned features individually or jointly contribute to various aspects of the realization of a low power-consumption, intraluminally sized control devices which provide desired functionality in implantable medical devices.

In various aspects, the integrated circuit is characterized by having low power consumption while providing necessary functions for automated actuating or sensing, e.g., from multiple electrodes or sensors which may be coupled to the integrated circuit. Particularly, the modular components of the underlying integrated circuit and related circuitry consume significantly reduced amounts of power, e.g., as compared to non-integrated circuits that may include similar functionalities, thereby allowing the entire implantable pacing/sensing system with which the integrated circuit is associated to operate with limited power source, such as may be provided by a battery included in a pacing can.

According to various aspects, the average power consumption of each integrated circuit is about 100 µW or less, such as about 100 nW or less, and including about 50 pW or less. The average current draw of the inventive integrated circuit while maintaining its configuration state is about 1 nA or less, including about 5 pA or less. In addition, the average current draw of the inventive integrated circuit when the configuration state of the device is being changed ranges from about 1 µA to about 100 µA, such as from about 10 µA to about 50 µA, and including from about 1 µA to about 20 µA.

In various aspects, the integrated circuit is associated with a number of electrodes, e.g., that may be present in a satellite structure of a lead, where multiple satellites may reside on a single implantable lead. The inventive implantable integrated circuits facilitate selecting and driving electrodes on such satellites and/or sensing signals through these electrodes. Furthermore, the inventive integrated circuits facilitate relaying data back from an electrode to a data collection system, so that the signals detected by the electrodes can be processed and analyzed. In such aspects, integrated circuits may also allow a satellite to maintain its configuration state once the satellite and its electrodes are configured. The satellites can retain their respective configuration states while the external power supply is turned off. Hence, the power consumption for the entire implantable signal administration/detection system can be significantly reduced compared with conventional systems.

The integrated circuits may include a number of additional functionalities imparted to the circuit by one or more additional functional blocks. All or just some of the components required for the following functionalities may be integrated into the circuit. As such, a given functional block as described above, is a functional block that, by itself or in conjunction with additional elements not integrated in the circuit, provides for the desired additional functionality. The functional blocks include a default mode functional block, a charge balanced operation functional block, a charge-balanced functional block, a multiplexer functional block, a fault tolerant functional block, an overvoltage and/or overcurrent functional block, an off-chip or on chip capacitor functional block, sleep functional block, and a wakeup functional block. In various aspects, these additional functionalities further enable the integrated circuits of the invention to have their intraluminal size and low power consumption and yet provide for desired functionality. Various examples of the above functional blocks are further described in PCT Application Serial No. PCT/US2006/048944 titled "Implantable Integrated Circuit" and filed on Dec. 22, 2006, the disclosure of which is herein incorporated by reference.

The integrated circuits of the invention find use in a variety of implantable devices and methods of using the same, where such devices include, but are not limited to, cardiac devices, neurological devices, etc. The circuits find use in implantable devices that include a control portion, and one or more satellite functionalities distal from the control portion, where the one or more satellite functionalities are in conductive communication with the control portion, e.g., via one or more two wires present in a lead. For description purposes only, the following description of various aspects focuses primarily on cardiac aspects, and particularly implantable pulse generator aspects. Although the following description frequently uses cardiac pacing as an exemplary application, various aspects can be applied by a wide range of applications wherein signals are administered to or detected from living tissues. Such applications include, but are not limited to: cardiac pacing and monitoring, neurological stimulation, bone growth stimulation, and drug delivery. It should be noted that integrated circuits of the invention may have one or more functional blocks that enable the following functionalities. However, the following functionalities are not limited to their implementation in the integrated circuits of the device, but could appear in other implantable medical devices and systems that may not include the integrated circuits as summarized above. These additional medical devices and systems to the extent they include one or more of the following functionalities are specifically within the scope of this invention.

To provide a useful context for the description of the cardiac device aspects, a general review of an implantable pulse generator system, vascular lead thereof a functional block diagram of an integrated circuit thereof is first provided. Following this section, further description of the integrated circuit aspects is provided.

Implantable Pulse Generators

Various aspects include implantable pulse generators. Implantable pulse generators may include: a housing which includes a power source and an electrical stimulus control element; one or more vascular leads as described above, e.g., 2 or more vascular leads, where each lead is coupled to the control element in the housing via a suitable connector, e.g., an IS-1 connector. In various aspects, the implantable pulse generators are ones that are employed for cardiovascular applications, e.g., pacing applications, cardiac resynchronization therapy applications, etc. As such, in various aspects the control element is configured to operate the pulse generator in a manner so that it operates as a pacemaker, e.g., by having an appropriate control algorithm recorded onto a computer readable medium of a processor of the control element. In various aspects the control element is configured to operate the pulse generator in a manner so that it operates as a cardiac resynchronization therapy device, e.g., by having an appropriate control algorithm recorded onto a computer readable medium of a processor of the control element.

An implantable pulse generator according to various aspects of the invention is depicted in FIG. 1. FIG. 1 illustrates the locations of a number of pacing satellites incorporated in multi-electrode pacing leads, in accordance with various aspects. A pacing and signal detection system 101 provides extra-cardiac communication and control elements for the overall system. In various aspects, pacing and signal detection system 101 may be, for example, a pacing can of a pacemaker residing in an external or extra-corporeal location.

Right ventricular lead 102 emerges from pacing and signal detection system 101 and travels from a subcutaneous location from pacing and signal detection system 101 into the patient's body (e.g., preferably, a subclavian venous access), and through the superior vena cava into the right atrium. From the right atrium, right ventricle lead 102 is threaded through the tricuspid valve to a location along the walls of the right ventricle. The distal portion of right ventricular lead 102 is preferably located along the intra-ventricular septum, terminating with a fixation in the right ventricular apex. Right ventricular lead 102 includes satellites positioned at locations 103 and 104. The number of satellites in ventricular lead 102 is not limited, and may be more or less than the number of satellites shown in FIG. 1.

Similarly, left ventricular lead 105 emerges from pacing and signal detection system 101, following substantially the same route as right ventricular lead 102 (e.g., through the subclavian venous access and the superior vena cava into the right atrium). In the right atrium, left ventricular lead 105 is threaded through the coronary sinus around the posterior wall of the heart in a cardiac vein draining into the coronary sinus. Left ventricular lead 105 is provided laterally along the walls of the left ventricle, which is likely to be an advantageous position for bi-ventricular pacing. FIG. 1 shows satellites positioned at locations 106 and 107 along left ventricular lead 105. Right ventricular lead 102 may optionally be provided with pressure sensor 108 in the right ventricle. A signal multiplexing arrangement allows a lead to include such active devices (e.g., pressure sensor 108) for pacing and signal collection purposes (e.g., right ventricular lead 102). Pacing and signal detection system 101 communicates with each of the satellites at locations 103, 104, 106 and 107. The electrodes controlled by the satellites may also be used to detect cardiac depolarization signals. Additionally, other types of sensors, such as an accelerometer, strain gauge, angle gauge, temperature sensor, can be included in any of the leads.

In the above system, the device components can be connected by a multiplex system (e.g., as described in published United States Patent Application publication nos.: 20040254483 titled "Methods and systems for measuring cardiac parameters"; 20040220637 titled "Method and apparatus for enhancing cardiac pacing"; 20040215049 titled "Method and system for remote hemodynamic monitoring"; and 20040193021 titled "Method and system for monitoring and treating hemodynamic parameters; the disclosures of which are herein incorporated by reference), to the proximal end of electrode lead 105. The proximal end of electrode lead 105 connects to a pacemaker 101, e.g., via an IS-1 connector.

During various aspects of use, the electrode lead 105 is placed in the heart using standard cardiac lead placement devices which include introducers, guide catheters, guidewires, and/or stylets. Briefly, an introducer is placed into the clavicle vein. A guide catheter is placed through the introducer and used to locate the coronary sinus in the right atrium. A guidewire is then used to locate a left ventricle cardiac vein. The electrode lead 105 is slid over the guidewire into the left ventricle cardiac vein and tested until an optimal location for CRT is found. Once implanted a multi-electrode lead 105 still allows for continuous readjustments of the optimal electrode location.

The electrode lead 102 is placed in the right ventricle of the heart. In this view, the electrode lead 102 is provided with one or multiple electrodes 103,104.

Electrode lead 102 is placed in the heart in a procedure similar to the typical placement procedures for cardiac right ventricle leads. Electrode lead 102 is placed in the heart using the standard cardiac lead devices which include introducers, guide catheters, guidewires, and/or stylets. Electrode lead 102 is inserted into the clavicle vein, through the superior vena cava, through the right atrium and down into the right ventricle. Electrode lead 102 is positioned under fluoroscopy into the location the clinician has determined is clinically optimal and logistically practical for fixating the electrode lead 102.

Summarizing aspects of the above description, in using the implantable pulse generators of the invention, such methods include implanting an implantable pulse generator e.g., as described above, into a subject; and the implanted pulse generator, e.g., to pace the heart of the subject, to perform cardiac resynchronization therapy in the subject, etc. The description of the present invention is provided herein in certain instances with reference to a subject or patient. As used herein, the terms "subject" and "patient" refer to a living entity such as an animal. In various aspects, the animals are "mammals" or "mammalian," where these terms are used broadly to describe organisms which are within the class mammalia, including the orders carnivore (e.g., dogs and cats), rodentia (e.g., mice, guinea pigs, and rats), lagomorpha (e.g. rabbits) and primates (e.g., humans, chimpanzees, and monkeys). In various aspects, the subjects, e.g., patients, are humans.

During operation, use of the implantable pulse generator may include activating at least one of the electrodes of the pulse generator to deliver electrical energy to the subject, where the activation may be selective, such as where the method includes first determining which of the electrodes of the pulse generator to activate and then activating the electrode. Methods of using an IPG, e.g., for pacing and CRT, are disclosed in Application Serial Nos.: PCT/US2005/031559 titled "Methods and Apparatus for Tissue Activation and Monitoring," filed on Sep. 1, 2006; PCT/US2005/46811 titled "Implantable Addressable Segmented Electrodes" filed on Dec. 22, 2005; PCT/US2005/46815 titled "Implantable Hermetically Sealed Structures" filed on Dec. 22, 2005; and Ser. No. 11/734,617 titled "High Phrenic, Low Capture Threshold Pacing Devices and Methods," filed Apr. 12, 2006; the disclosures of the various methods of operation of these applications being herein incorporated by reference and applicable for use of the present devices.

Various aspects of the invention further include electrode assemblies, such as electrode satellite structures, where the structures include an integrated circuit control device, e.g., including a circuit of the present invention (described more fully below), and at least one electrode element. As such, the satellite structures include control circuitry, e.g., in the form of an IC (e.g., an IC inside of the support), such that the satellite structure is addressable. In various aspects, the structure includes two or more electrode elements, such as three or more electrode elements, including four or more electrode elements, e.g., where the structure is a segmented electrode structure.

As reviewed above, the integrated circuit may be hermetically sealed or protected. Various aspects of hermetically sealed IC chips include, but are not limited to, those described in PCT application serial PCT/US2005/046815 titled "Implantable Hermetically Sealed Structures" and filed on Dec. 22, 2005; and PCT application serial PCT/US2007/009270 titled "Void-Free Implantable Hermetically Sealed Structures" and filed on Apr. 12, 2007 (PRTS-040WO); the descriptions of hermetically sealed structures provided in these applications being specifically incorporated herein by reference.

As summarized above, various aspects provide implantable medical devices that include the electrode structures as described above. By implantable medical device is meant a device that is configured to be positioned on or in a living body, where in various aspects the implantable medical device is configured to be implanted in a living body. Various aspects of the implantable devices are configured to maintain functionality when present in a physiological environment, including a high salt, high humidity environment found inside of a body, for 2 or more days, such as about 1 week or longer, about 4 weeks or longer, about 6 months or longer, about 1 year or longer, e.g., about 5 years or longer. In various aspects, the implantable devices are configured to maintain functionality when implanted at a physiological site for a period ranging from about 1 to about 80 years or longer, such as from about 5 to about 70 years or longer, and including for a period ranging from about 10 to about 50 years or longer. The dimensions of the implantable medical devices of the invention may vary. However, because the implantable medical devices are implantable, the dimensions of various aspects of the devices are not so big such that the device cannot be positioned in an adult human.

Various aspects also include medical carriers that include one or more electrode satellite structures, e.g., as described above. Carriers of interest include, but are not limited to, vascular lead structures, where such structures are generally dimensioned to be implantable and are fabricated from a physiologically compatible material. With respect to vascular leads, a variety of different vascular lead configurations may be employed, where the vascular lead in various aspects is an elongated tubular, e.g., cylindrical, structure having a proximal and distal end. The proximal end may include a connector element, e.g., an IS-1 connector, for connecting to a control unit, e.g., present in a "can" or analogous device. The lead may include one or more lumens, e.g., for use with a guidewire, for housing one or more conductive elements, e.g., wires, etc. The distal end may include a variety of different features as desired, e.g., a securing means, etc.

In various aspects of the subject systems, one or more sets of electrode assemblies or satellites as described above are electrically coupled to at least one elongated conductive member, e.g., an elongated conductive member present in a lead, such as a cardiovascular lead. For example, two or more assemblies are coupled to a common at least one electrical conductor, i.e., to the same at least one electrical conductor. In various aspects, the elongated conductive member is part of a multiplex lead. Multiplex lead structures may include 2 or more satellites, such as 3 or more, 4 or more, 5 or more, 10 or more, 15 or more, 20 or more, etc. as desired, where in various aspects multiplex leads have a fewer number of conductive members than satellites. In various aspects, the multiplex leads include 3 or less wires, such as only 2 wires or only 1 wire. Multiplex lead structures of interest include those described in application Ser. No. 10/734,490 titled "Method and System for Monitoring and Treating Hemodynamic Parameters" filed on Dec. 11, 2003; PCT/US2005/031559 titled "Methods and Apparatus for Tissue Activation and Monitoring," filed on Sep. 1, 2006; PCT/US2005/46811 titled "Implantable Addressable Segmented Electrodes" filed on Dec. 22, 2005; PCT/US2005/46815 titled "Implantable Hermetically Sealed Structures" filed on Dec. 22, 2005; and Ser. No. 11/734,617 titled "High Phrenic, Low Pacing Capture Threshold Pacing Devices and Methods" filed Apr. 12, 2007; the disclosures of the various multiplex lead structures of these applications being herein incorporated by reference. In various aspects, the devices and systems may include onboard logic circuitry or a processor, e.g., present in a central control unit, such as a pacemaker can. In these aspects, the central control unit may be electrically coupled to the lead by a connector, such as a proximal end IS-1 connection.

Figure 2:
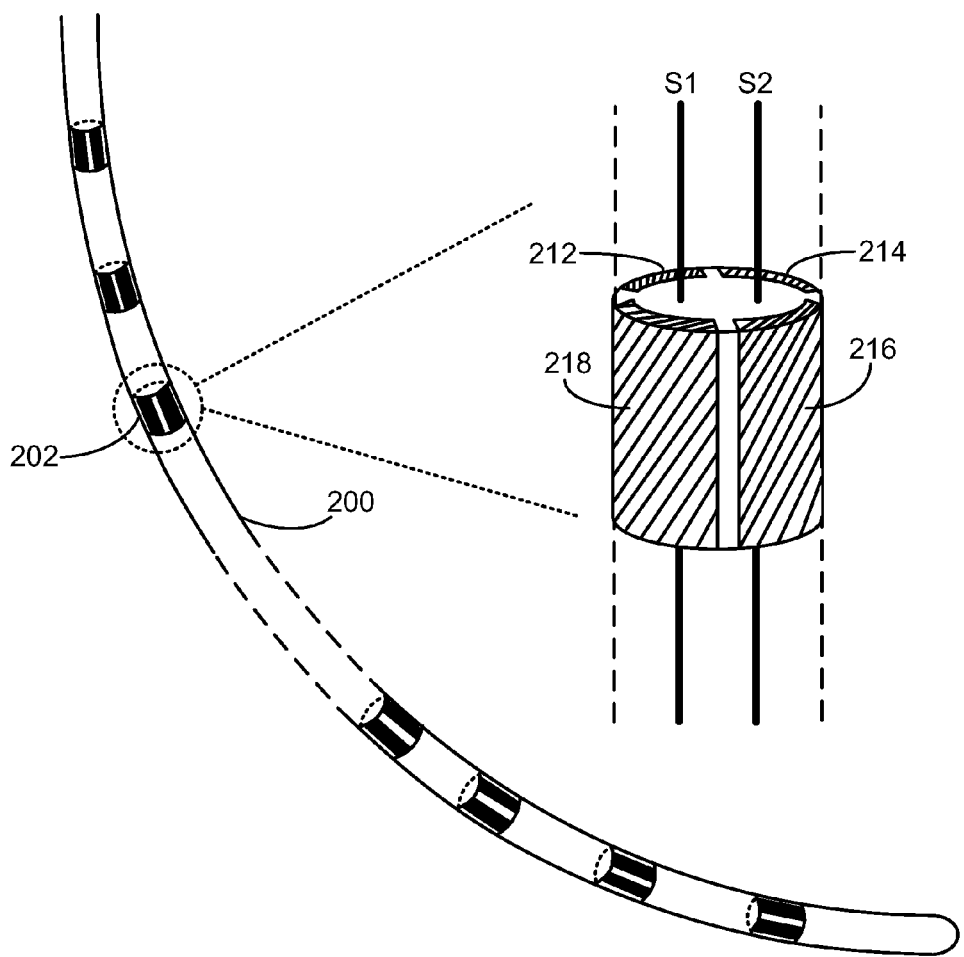
FIG. 2 illustrates an exemplary external view of a number of pacing satellites, in accordance with various aspects of the present invention.

FIG. 2 illustrates an external view of a number of exemplary pacing satellites, in accordance with multiplex lead aspects of the present invention. According to various aspects, a pacing lead 200 (e.g., right ventricular lead 102 or left ventricular lead 105 of FIG. 1) accommodates two bus wires S1 and S2, which are coupled to a number (e.g., eight) of satellites, such as satellite 202. FIG. 2 also shows satellite 202 with an enlarged view. Satellite 202 includes electrodes 212, 214, 216, and 218, located in the four quadrants of the cylindrical outer walls of satellite 202 and supported by a support structure of the invention. Each satellite also contains a control chip inside the structure which communicates with a pacing and signal-detection system to receive configuration signals that determine which of the four electrodes are to be coupled to bus wires S1 or S2.

The configuration signals, the subsequent pacing pulse signals, and the analog signals collected by the electrodes can all be communicated through bus wires S1 and S2, in either direction. Although shown in a symmetrical arrangement, electrodes 212, 214, 216 and 218 may be offset along lead 200 to minimize capacitive coupling among these electrodes. The quadrant arrangement of electrodes allows administering pacing current via electrodes oriented at a preferred direction, for example, away from nerves, or facing an electrode configured to sink the pacing current. Such precise pacing allows low-power pacing and minimal tissue damage caused by the pacing signal.

The leads may further include a variety of different effector elements, which elements may employ the satellites or structures distinct from the satellites. The effectors may be intended for collecting data, such as but not limited to pressure data, volume data, dimension data, temperature data, oxygen or carbon dioxide concentration data, hematocrit data, electrical conductivity data, electrical potential data, pH data, chemical data, blood flow rate data, thermal conductivity data, optical property data, cross-sectional area data, viscosity data, radiation data and the like. As such, the effectors may be sensors, e.g., temperature sensors, accelerometers, ultrasound transmitters or receivers, voltage sensors, potential sensors, current sensors, etc. Alternatively, the effectors may be intended for actuation or intervention, such as providing an electrical current or voltage, setting an electrical potential, heating a substance or area, inducing a pressure change, releasing or capturing a material or substance, emitting light, emitting sonic or ultrasound energy, emitting radiation and the like.

Effectors of interest include, but are not limited to, those effectors described in the following applications by at least some of the inventors of the present application: U.S. patent application Ser. No. 10/734,490 published as 20040193021 titled: "Method And System For Monitoring And Treating Hemodynamic Parameters"; U.S. patent application Ser. No. 11/219,305 published as 20060058588 titled: "Methods And Apparatus For Tissue Activation And Monitoring"; International Application No. PCT/US2005/046815 titled: "Implantable Addressable Segmented Electrodes"; U.S.

patent application Ser. No. 11/324,196 titled "Implantable Accelerometer-Based Cardiac Wall Position Detector"; U.S. patent application Ser. No. 10/764,429, entitled "Method and Apparatus for Enhancing Cardiac Pacing," U.S. patent application Ser. No. 10/764,127, entitled "Methods and Systems for Measuring Cardiac Parameters," U.S. patent application Ser. No. 10/764,125, entitled "Method and System for Remote Hemodynamic Monitoring"; International Application No. PCT/US2005/046815 titled: "Implantable Hermetically Sealed Structures"; U.S. application Ser. No. 11/368, 259 titled: "Fiberoptic Tissue Motion Sensor"; International Application No. PCT/US2004/041430 titled: "Implantable Pressure Sensors"; U.S. patent application Ser. No. 11/249, 152 entitled "Implantable Doppler Tomography System," and claiming priority to: U.S. Provisional Patent Application No. 60/617,618; International Application Serial No. PCT/USUS05/39535 titled "Cardiac Motion Characterization by Strain Gauge". These applications are incorporated in their entirety by reference herein.

Figure 3:
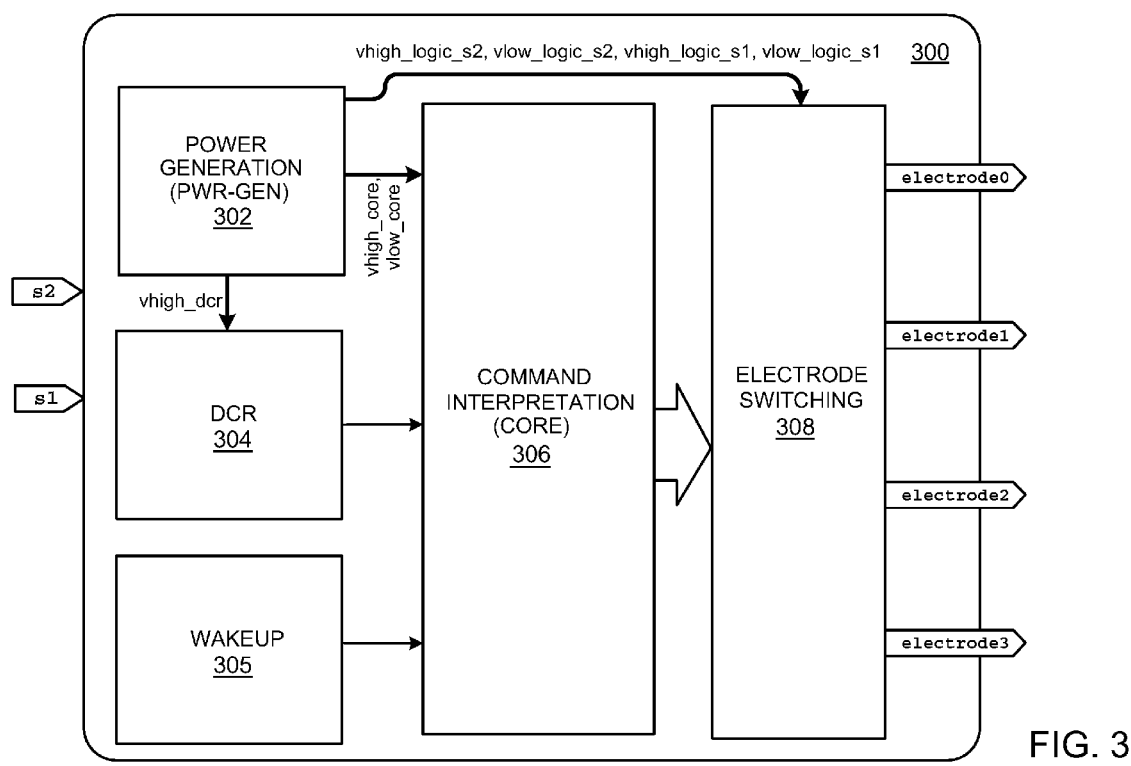
FIG. 3 is a high-level block diagram for a control circuitry within a satellite on a multi-satellite lead, in accordance with various aspects of the present invention.

FIG. 3 is a high-level block diagram for an integrated circuit of various aspects of the invention that includes control circuitry for a satellite structure that may be present on a multi-satellite lead, in accordance with various aspects. Control circuit 300 includes a power generation (PWR-GEN) module 302 (which is a power extraction block), a data-clock recovery (DCR) module 304, a wakeup module 305, a command interpretation module 306 (referred to as the "CORE" module in various aspects), and an electrode-switching module 308 which is coupled to four electrodes.

DCR module 304 provides the correct clock signals recovered from signals, as may be carried on bus wires S1 and S2 (See e.g., FIG. 2 described in greater detail below) to the rest of digital circuitry within control chip 300. DCR module 304 also recovers the data signals carried on S1 and S2 into a digital format that can be used by CORE module 306.

Wakeup module 305 generates a wakeup signal to activate and initialize other modules after a dormant period during which circuits within control chip 300 are turned off to preserve power.

CORE module 306 generates the proper control signals, based on the data received from DCR module 304, to control electrode-switching module 308. Electrode-switching module 308 then selects and switches the electrodes so that the desired electrodes can couple to S1 or S2 for pacing and/or signal-detection purposes.

PWR-GEN module 302 generates the power-supply voltages for CORE module 306, DCR module 304, and electrode-switching module 308. Specifically, PWR-GEN module 302 provides two voltages, vhigh_core and vlow_core, to CORE module 306, and a high voltage, vhigh_dcr, to DCR module 304. Furthermore, PWR-GEN module 302 provides four switch-control signals, vhigh_logic_S2, vlow_logic_s2, vhigh_logic_S1, and vlow_logic_s1, to electrode-switching module 308. These four switch-control signals ensure the electrode-switching circuits to turn on or off sufficiently under large S2-S1 voltage swings incurred during charge-balanced pacing.

Data Encoding Interface

An interface for communicating from an implantable cardio-defibrillator (ICD) circuit to an IC located in a vascular lead electrode satellite can involve defined symbols to accommodate data and/or command conveyance. The symbols can be encoded in the ICD, transmitted via interconnecting wires to a satellite, and then decoded within the satellite device in order to ascertain the particular communicated bits of information, and thus any associated data or commands. Such a data encoding interface is described herein in terms of: (i) interface waveforms showing interface and related signal operation; (ii) demodulation circuitry for decoding or recovering the encoded data in the satellite IC; and (iii) data encoding methods.

In order to reduce overall system size and complexity relative to conventional approaches, a simplified data encoding interface having one signal for data encoding and another signal for a common ground connection can be used. Because no separate clock signal is utilized, and because no separate reference signal need be used for data recovery, such an interface approach may be referred to as "self-clocking" and "self-referencing." Using this approach, the encoding of data signals for transmission to remote devices can substantially reduce the size and complexity of the system relative to directly transmitted data approaches.

For example, a form of phase shift keying (PSK) can be utilized to accomplish a self-referencing and self-clocking interface approach. Other approaches, including amplitude shift keying (ASK), or other suitable forms of modulation, may also be used to encode data in various aspects, and in some cases can be used in conjunction with PSK-like approaches. However, ASK modulation typically uses multiple voltage sources to generate different amplitudes, and these can be subject to variation, resulting in lower reliability as compared to PSK approaches. In various aspects, four symbols can be used in communication between circuits, such as between an ICD circuit and an IC located in a vascular lead electrode satellite, which may be in a multi-electrode lead (MEL) coupled to the ICD.

In various aspects, a single wire plus a ground connection can be utilized for data encoding in communication from an ICD to a satellite. Further, such ground connections may be coupled via a terminal to a human body. The single wire can be utilized to essentially encode clock and data signals. Thus, no separate clock signal need be transmitted. For demodulation, a data clock recovery (DCR) circuit can be utilized in the satellite to derive communicated symbols without the aid of a separately-supplied clock signal. In one particular example, the symbols may each be conveyed over a time period of six time intervals. Of course, other numbers of time intervals can also be utilized in various aspects. Here, a simplified and robust implementation can include a same "1010" pattern for symbol transmission, where each high or low phase is maintained for approximately one or two time intervals. This can allow for symbol patterns in the transmitted signals to be driven from a same clock source, resulting in further simplification.

For example, a preferred time interval is about 0.5 µs (500 ns), thus two time intervals can have a total duration of about 1 µs (1,000 ns). Any suitable time interval and/or pulse or signal state durations can be accommodated in various aspects. Time intervals can be in a range of from about 200 ns to about 800 ns, such as from about 250 ns to about 750 ns, and including from about 400 ns to about 600 ns. As technology improves, the time intervals can even decrease by orders of magnitude (e.g., into the tens of nanoseconds, or less, range). Generally, various aspects can support increased operating margins for a more robust solution. Further, approaches as described herein are applicable to any two-line or minimum communication bus with type of communication between two or more devices.

Implantable Bidirectional Communicator System Arrangements/Circuitry

In the present bidirectional communication system for implantable devices, encoded data transmission from a controller to a satellite device, as well as return communication from a selected satellite device to the controller, can include a minimized two wire interface, as discussed above. Generally, the encoded data transmissions are predefined symbols that may be demodulated within a satellite device for determination of particular conveyed commands, data bits, or the like. Further, a talkback mode can accommodate data transmission from a selected satellite device to the controller. When in talkback mode, the selected satellite device provides a series of data bits using a form of ASK for modulation. Such a series of data bits can include a configuration status of electrodes coupled to an IC in the satellite device. Further, sensing circuitry in the controller can be used to detect communicated bit values (e.g., '0' or '1'), each representing a particular state or configuration of an electrode.

Figure 4:
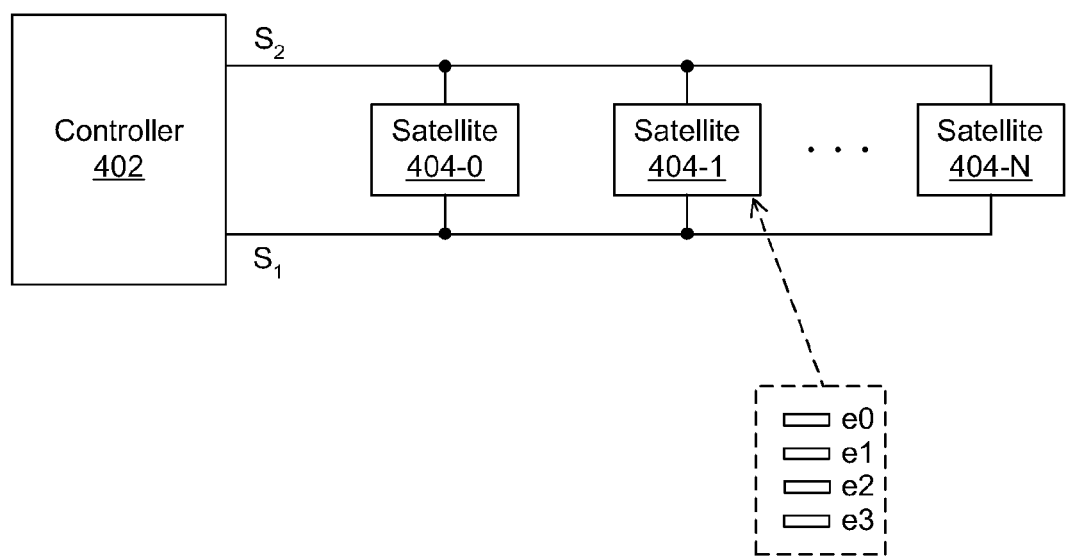
FIG. 4 illustrates an exemplary implantable satellite and controller arrangement suitable for bidirectional communication in accordance with various aspects of the present invention.

FIG. 4 shows an exemplary implantable satellite and controller arrangement suitable for bidirectional communication in accordance with various aspects of the present invention. Controller 402 can be an ICD, and may be coupled to any number of satellite devices (e.g., satellites 404-0, 404-1, . . . 404-N) via lead lines $S_1$ and $S_2$ (e.g., in an MEL). Each satellite may have electrodes therein, or may be otherwise coupled to electrodes (e.g., e0, e1, e2, and e3). While only four electrodes are shown in this particular example, any suitable number of electrodes can be accommodated. In addition, each individual satellite device can be selected based on a pre-assigned or predetermined address for each device. For example, satellite 404-0 can have a predetermined address of "000," satellite 404-1 can have a predetermined address of "001," and so on. As will be discussed in more detail below, these addresses can be conveyed from controller 402 to a selected satellite device 404 using encoded data symbols.

Generally, controller 402 can send a signal that includes a command and an address along wires $S_1/S_2$, and a selected satellite 404 (e.g., based on a match to the address) can respond using the same wires $S_1/S_2$. Further, the commands, addresses, and/or any other suitable data transmitted from controller 402 to satellites 404 can include one or more encoded symbols. Among the possible command types are "switch," "clear," "sleep," "default check," and "talkback." A talkback mode can be entered in response to transmission of a predetermined set of symbols, resulting in a predetermined time period in which the selected satellite device can provide configuration and/or status information to controller 402. As an alternative to an address followed by a corresponding command, any number of addresses followed by any number of commands (e.g., 5 addresses followed by 5 commands) in a communication stream.

Interface Waveforms

Various example waveforms illustrating a data encoding interface operation in various aspects will be shown and discussed below. These example waveforms primarily show data encoding from a controller to a satellite IC device (e.g., FIGS. 5-6), and then data recovery within that satellite IC device (e.g., FIG. 7).

Figure 5:
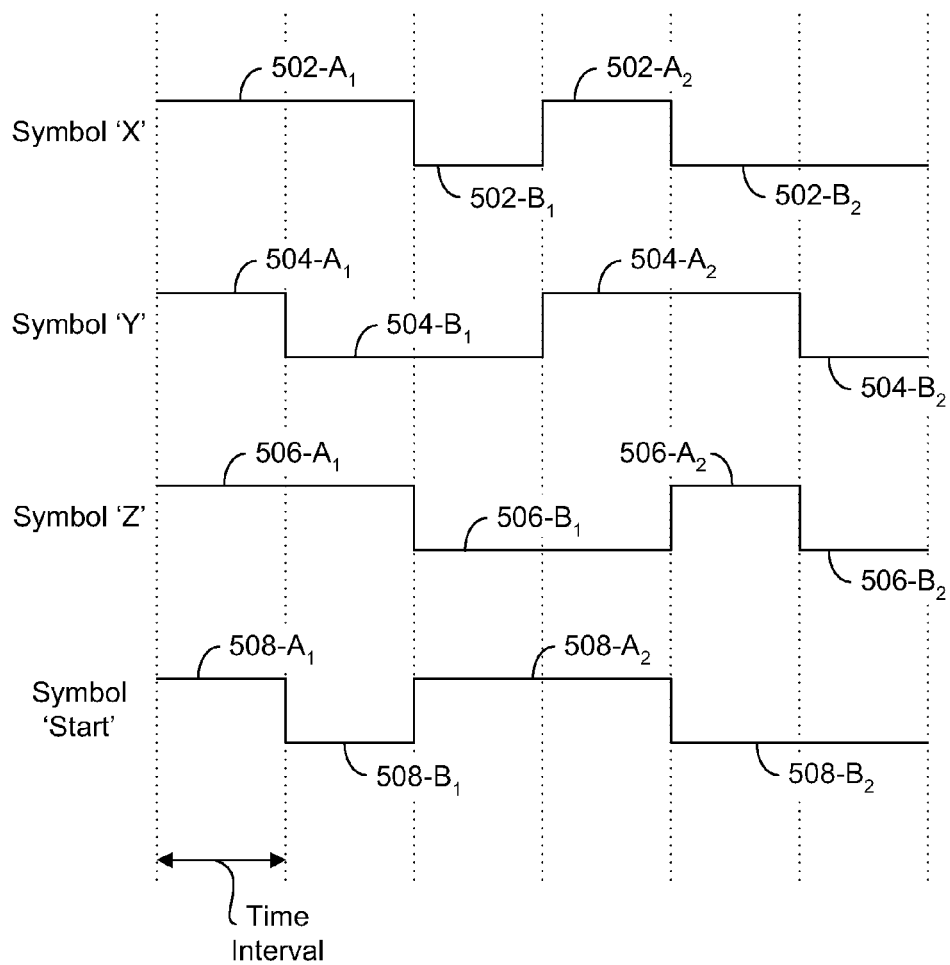
FIG. 5 illustrates timing waveforms for data encoding in accordance with various aspects of the present invention.

Referring now to FIG. 5, timing waveforms for data encoding in accordance with various aspects of the present invention are shown. Symbol 'X' can be encoded as a first high phase 502-$A_1$ lasting for two time intervals, then a first low phase 502-$B_1$ lasting for one time interval, then a second high phase 502-$A_2$ lasting for one time interval, followed by a second low phase 502-$B_2$ lasting for two time intervals, for a total of six time intervals. Thus, symbol X can be demodulated by a phase or pulse duration comparison, as shown below in Equation 1.

$$X: A_1 > A_2 \text{ and } B_1 < B_2 \quad (1)$$

Symbol 'Y' can be encoded as a first high phase 504-$A_1$ lasting for one time interval, then a first low phase 504-$B_1$ lasting for two time intervals, then a second high phase 504-$A_2$ lasting for two time intervals, followed by a second low phase 504-$B_2$ lasting for one time interval, for a total of six time intervals. Thus, symbol Y can be demodulated by a phase or pulse duration comparison, as shown below in Equation 2.

$$Y: A_1 < A_2 \text{ and } B_1 > B_2 \quad (2)$$

Symbol 'Z' can be encoded as a first high phase 506-$A_1$ lasting for two time intervals, then a first low phase 506-$B_1$ lasting for two time intervals, then a second high phase 506-$A_2$ lasting for one time interval, followed by a second low phase 506-$B_2$ also lasting for one time interval, for a total of six time intervals. Thus, symbol Z can be demodulated by a phase or pulse duration comparison, as shown below in Equation 3.

$$Z: A_1 > A_2 \text{ and } B_1 > B_2 \quad (3)$$

A 'Start' symbol can be utilized to indicate to the satellites that a control sequence is set to begin. For example, Start can be encoded as a first high phase 508-$A_1$ lasting for one time interval, then a first low phase 508-$B_1$ also lasting for one time interval, then a second high phase 508-$A_2$ lasting for two time intervals, followed by a second low phase 508-$B_2$ also lasting for two time intervals, for a total of six time intervals. Thus, symbol Start can be demodulated by a phase or pulse duration comparison, as shown below in Equation 4.

$$Start: A_1 < A_2 \text{ and } B_1 < B_2 \quad (4)$$

Binary data can then be decoded from sequential symbols, where symbol pairs may be identified in relation to the Start symbol (e.g., such symbol pairs may follow a Start symbol). Table 1 below shows one example of binary coded data relative to symbol pairs. Of course, additional symbols strung together can allow for longer binary strings, and expansion of the table shown. Further, other symbol definitions, and corresponding binary data bit values can also be accommodated in various aspects.

TABLE 1

| Symbols | Binary Data |
| --- | --- |
| XY | 000 |
| YZ | 001 |
| XX | 010 |
| XZ | 011 |
| YY | 100 |
| ZY | 101 |
| ZX | 110 |
| ZZ | 111 |
| YX | error |

Other approaches to data encoding suitable for implantable devices can include where each signal phase defines a particular bit position, and each subsequent phase has a duration of half the previous phase. However, such an approach typically requires comparison to a known reference or group of references, which can be a relatively difficult implementation. In self-referencing approaches of various aspects, values or phases can simply be compared against each other. Thus, no separate reference may be needed, and the overall circuit complexity can be substantially reduced.

Figure 6:
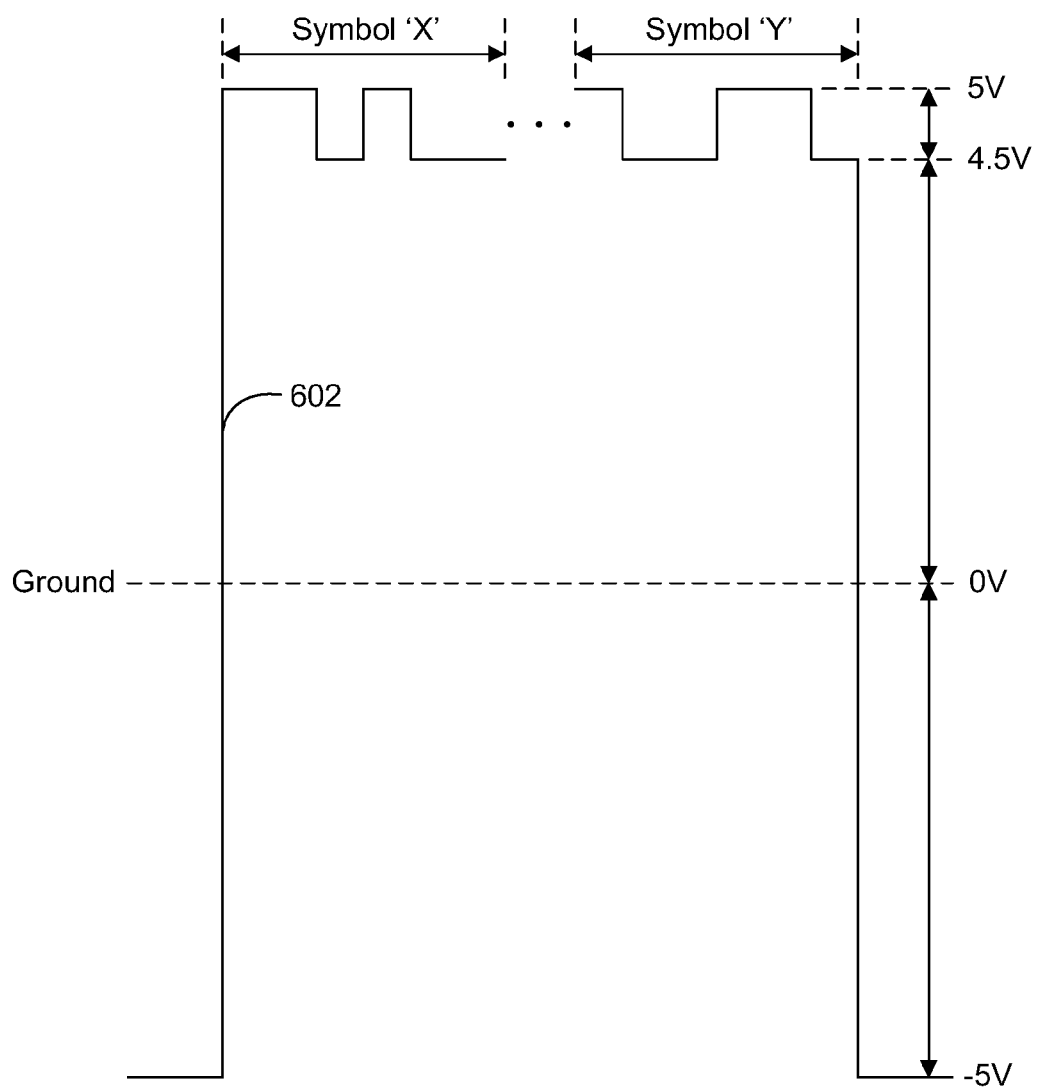
FIG. 6 illustrates a full-swing waveform for data encoding in accordance with various aspects of the present invention.

Referring now to FIG. 6, a full-swing waveform for data encoding in accordance with various aspects of the present invention is shown. Waveform 602 can be driven by an ICD, and received by a satellite IC, as discussed above. In various aspects, data encoding of symbols (e.g., symbols X and Y) can be accomplished as a relatively small swing voltage variation on a larger voltage level. For example, waveform 602 can range from about −5 V to about 4.5 V, and then between about 4.5 V and 5 V to support data encoding. Accordingly, a "low phase" as discussed above with reference to FIG. 5 can be about 4.5 V, while a "high phase" may be about 5 V, as shown in the particular example of FIG. 6.

The negative portion of waveform 602 can allow for charge balancing on this interface signal. Waveform 602 can represent a differential voltage (e.g., the voltage on lead line $S_2$ minus the voltage on lead line $S_1$). For this type of charge balancing, a negative portion of the signal can offset the positive portion by remaining at or near a negative rail (e.g., about −5 V) for approximately a same amount of time as the signal is at or near a positive rail (e.g., in the range from about 4.5 V to about 5 V). In this fashion, charge balance can be achieved on the signal interfacing between the ICD and one or more satellite devices in an MEL.

However, a negative voltage rail is not required for suitable charge balancing. For example, an "H-bridge" topology may be used for driving the $S_1$ and $S_2$ lead lines. In this approach, during communication, $S_1$ (or $S_2$) may be connected to ground, while lead line $S_2$ (or $S_1$) is at either about 4.5 V or about 5 V for signaling During charge balancing, $S_2$ (or $S_1$) may be at ground, while $S_1$ (or $S_2$) is held at about 5 V. This bi-polar signaling also helps to protect against inadvertent tissue capture in the event of mechanical failure in a satellite device. This may be of concern for applications including control of a pressure transducer, or other non-pacing type functions.

Of course, any suitable voltage levels can be utilized for the "rails," as well as the low/high phase supplies. For example, various aspects can utilize voltages having absolute values in a range of from about 1.5 V to about 8 V, such as from about 1.8 V to about 7.5 V, including from about 2.5 V to about 6.5 V, and including from about 3.3 V to about 6V, yet preferably about 5 V. Further, any such lower voltages as future low-voltage technology implementations may allow, or any such higher voltages as particular technologies (e.g., supporting transistor breakdown voltages), particular applications, etc., may allow, can also be accommodated in various aspects.

Figure 7:
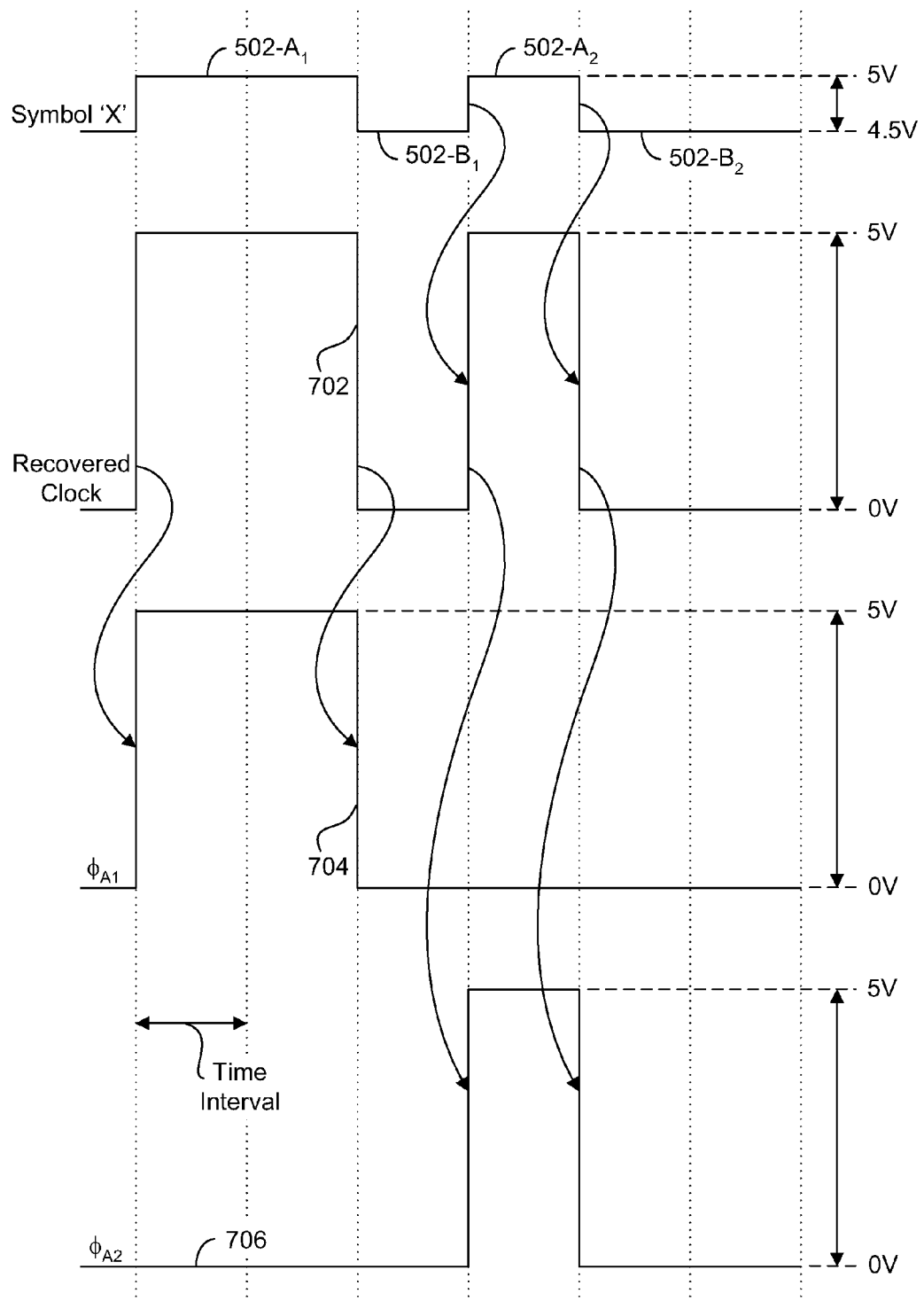
FIG. 7 illustrates exemplary recovered clock and phase control signal waveforms in accordance with various aspects of the present invention.

Referring now to FIG. 7, exemplary recovered clock and phase control signal waveforms in accordance with various aspects of the present invention are shown. Signal delays in generating the recovered clock and phase control signals are not shown herein for simplicity. Following the example discussed above with reference to FIG. 5, symbol X is shown as ranging from about 4.5 V to about 5 V with phases 502-$A_1$, 502-$B_1$, 502-$A_2$, and 502-$B_2$. Of course, as discussed above, supply values of 4.5 V, 5 V, etc., are merely exemplary, and any suitable supply voltage can be utilized in various aspects.

In a DCR circuit, which can be located in an IC of a satellite device, recovered clock (waveform 702) can essentially be a full-swing (i.e., rail-to-rail) version of the received signal (e.g., symbol X). Thus, the recovered clock can range from a ground level (e.g., about 0 V) to a supply level (e.g., about 5 V). A first phase control signal, $\phi_{A1}$ (waveform 704), can then be generated from the first high pulse of recovered clock 702. Similarly, a second phase control signal, $\phi_{A2}$ (waveform 706), can be generated from the second high pulse of recovered clock 702.

In this fashion, first and second phase control signals $\phi_{A1}$ (waveform 704) and $\phi_{A2}$ (waveform 706) can be derived to correspond to first and second high phases (e.g., 502-$A_1$ and 502-$A_2$, respectively) of a received symbol. Although not shown, another version (e.g., an inversion or separately derived signal) of recovered clock 702 can be used to generate similar phase control signals for first and second low phases (e.g., 502-$B_1$ and 502-$B_2$) of the received symbol. Then, phase control signal pairs (e.g., $\phi_{A1}$ and $\phi_{A2}$) can be compared to determine which of the first or second high phases (e.g., 502-$A_1$ or 502-$A_2$) or pulse durations is longer. As shown above in Equations 1-4, these comparisons can be utilized to determine which symbol is being communicated in various aspects.

In performing this comparison, various aspects can allow for substantial margin for error because a 2:1 ratio of pulse width durations may be used in the original symbol transmission. Thus, derived phase control signal pairs (e.g., $\phi_{A1}$ and $\phi_{A2}$) can also differ in pulse width durations by the same, or a similar, ratio. For example, second phase control signal $\phi_{A2}$ (waveform 706) can have a pulse duration of about one time interval, while first phase control signal $\phi_{A1}$ (waveform 704) may have a pulse duration of about two time intervals. Of course, other ratios (e.g., in a range of ratios from about 1.2:1 to about 5:1, such as from about 1.4:1 to about 4:1, and including from about 1.6:1 to about 3:1) can be utilized in various aspects, as particular design constraints and margins will allow.

Demodulation Circuitry

In order to decode or recover the encoded data received from a controller in a satellite IC, demodulation circuitry (e.g., DCR circuitry) can be utilized. Located in the satellite IC, this circuitry can essentially receive encoded data signals, and produce binary data output, such as that shown above in Table 1. In various aspects, a simplified (e.g., having relatively few components) and robust (e.g., having relatively wide operating margins) circuit can be employed.

Figure 8:
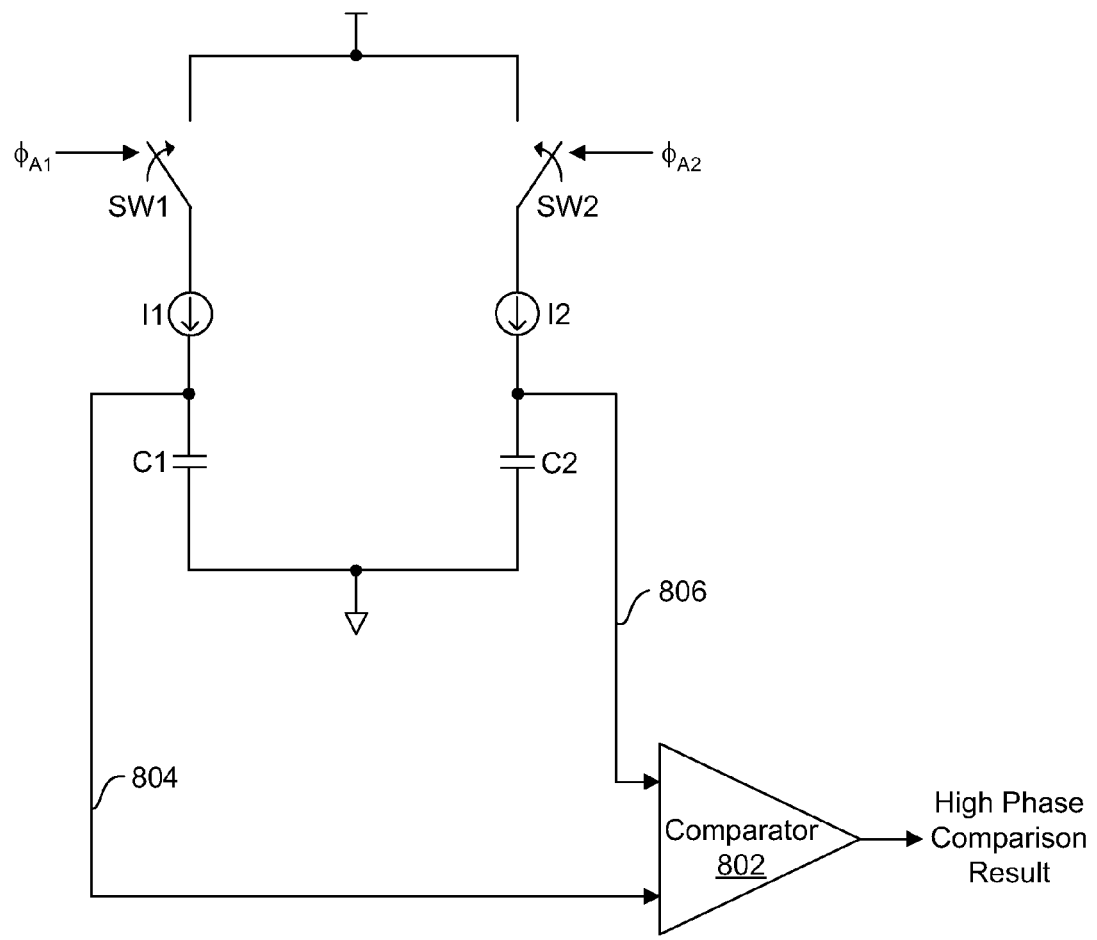
FIG. 8 illustrates an exemplary simplified DCR circuit portion in accordance with various aspects of the present invention.

Referring now to FIG. 8, an exemplary simplified DCR circuit portion in accordance with various aspects of the present invention is shown. First and second phase control signals (e.g., $\phi_{A1}$ and $\phi_{A2}$, with example waveforms 704 and 706, respectively, and as shown above in FIG. 7), can be applied to control switches SW1 and SW2. For example, if switches SW1 and SW2 are implemented as metal oxide semiconductor (MOS) transistors, signals $\phi_{A1}$ and $\phi_{A2}$ may be coupled to the respective transistor gates to allow current to pass from transistor source to transistor drain when asserted. Current sources I1 and I2 may also be implemented as transistors (e.g., MOS transistors biased in saturation mode).

Current sources I1 and I2 can be respectively coupled to capacitors C1 and C2 in order to charge the associated capacitor when the corresponding phase control signal (e.g., $\phi_{A1}$ or $\phi_{A2}$) is high. In various aspects, capacitor values C1 and C2, as well as current source values I1 and I2, can be substantially the same in order to provide circuit balance. However, any of these values may be altered in order to enhance sensing margin corresponding to one of the phase control signals. Toward this end, capacitors C1 and C2, and current sources I1 and I2, can be modified by any suitable product characterization approach. For example, metal layer options, register-based controls, laser fuses, etc., can be used for adjusting these values. Current sources I1 and I2 can, for example, utilize resisters that may be added or removed by metal options, or any other suitable approach for such adjustment. Similarly, capacitors C1 and C2 can include capacitor portions (e.g., MOS capacitors) that can be added or removed from a parallel configuration by metal options or any other suitable approach for adjustment.

In various aspects, capacitance values for C1 and C2 can preferably be about 1 pF, but may suitably be, for example, any value in a range of from about 0.2 pF to about 2 pF, such as from about 0.5 pF to about 1.5 pF, and including from about 0.8 pF to about 1.2 pF. Also, resistance values for current sources I1 and I2 can preferably be about 400 KΩ, but may suitably be, for example, any value in a range of from about 100 KΩ to about 750 KΩ, such as from about 200 KΩ to about 600 KΩ, and including from about 300 KΩ to about 500 KΩ. Further, such resistance and capacitance values are tunable or adjustable, and may also vary depending upon the frequency of communication or circuit operation.

In order to provide a high phase comparison result (e.g., corresponding to a determination of $A_1 > A_2$, as shown above in Equations 1 and 3, or $A_1 < A_2$, as shown above in Equations 2 and 4), comparator 802 can be used to compare node 804 versus node 806. A voltage level on node 804 can be dependent on a time that SW1 is closed (e.g., when $\phi_{A1}$ is high, such as for about 1 μs) to allow charging of capacitor C1 via current source I1. Similarly, a voltage level on node 806 can be dependent on a time that SW2 is closed (e.g., when $\phi_{A2}$ is high, such as for about 0.5 μs) to allow charging of capacitor C2 via current source I2.

Accordingly, voltage levels on nodes 804 and 806 correspond to phase or pulse durations (e.g., 502-A$_1$ and 502-A$_2$, respectively), and the high phase comparison result output from comparator 802 can indicate which phase or pulse duration is longer (e.g., $A_1 > A_2$ or $A_1 < A_2$). Similar circuitry can be employed to provide a low phase comparison result to indicate whether $B_1 > B_2$ or $B_1 < B_2$). Digital logic can then be utilized to perform logic functions on the individual phase comparison results to determine if any of the defined symbols (e.g., X, Y, Z, or Start) has been received.

In various aspects, discharge circuitry (e.g., using a pull-down transistor) for capacitors C1 and C2 can also be used to effectively reset the circuit when neither $\phi_{A1}$ nor $\phi_{A2}$ is asserted. Alternatively, if the time period when neither $\phi_{A1}$ nor $\phi_{A2}$ is asserted is sufficiently long, C1 and C2 can simply be allowed to naturally discharge without the use of extra discharge circuitry. Further, other types of circuitry may be utilized in order to extend voltage margins (e.g., as related to ramp rates of $\phi_{A1}$ and $\phi_{A2}$) versus a supply voltage of comparator 802. For example, the voltage levels of nodes 804 and 806 may each be independently compared to a known reference level using two comparators.

As another example, comparator 802 can be used for an initial comparison, and then a comparison to a known reference level can be performed. Such a known reference level can be an intermediate reference level (e.g., about 2.5 V corresponding to a supply of about 5 V), and/or may utilize a "mimic" type of circuit to derive a suitable reference voltage. This approach can provide improved margin to accommodate situations where the supply of comparator 802 goes below the lower value of $\phi_{A1}$ or $\phi_{A2}$. Other approaches in various aspects can include current sensing, as opposed to voltage level detection.

Various aspects can also withstand substantial voltage level degradation over time due to relatively small signal swings of about 500 mV (above or below the corresponding supply or reference level), as compared to typical supply voltages of about 5 V. In addition, such supply voltages may also be programmable, similar to capacitors and current sources in the DCR circuit portion of FIG. 8. For example, metal layer options, register-based controls, laser fuses, etc., can be used for adjusting these values as part of the characterization process. Generally, adjustment may not be needed when one of nodes 804 or 806 is high relative to the supply voltage of comparator 802. Rather, of concern is if (e.g., due to pulse width and/or supply level variations) both of nodes 804 and 806 are high relative to the supply voltage of comparator 802. In this case, various aspects can allow for adjustments to be made to the supply voltage of comparator 802, as well as to capacitors C1/C2, and current sources I1/I2, as may be necessary to improve operating margins.

Data Encoding Methods

Using the simplified data encoding interface discussed above, methods of encoding data and sending that encoded data from a controller device to a satellite IC device, where demodulation/recovery can occur, will now be discussed. Using these methods along with the circuitry and interface described herein can support a simplified and robust interface approach.

Figure 9:
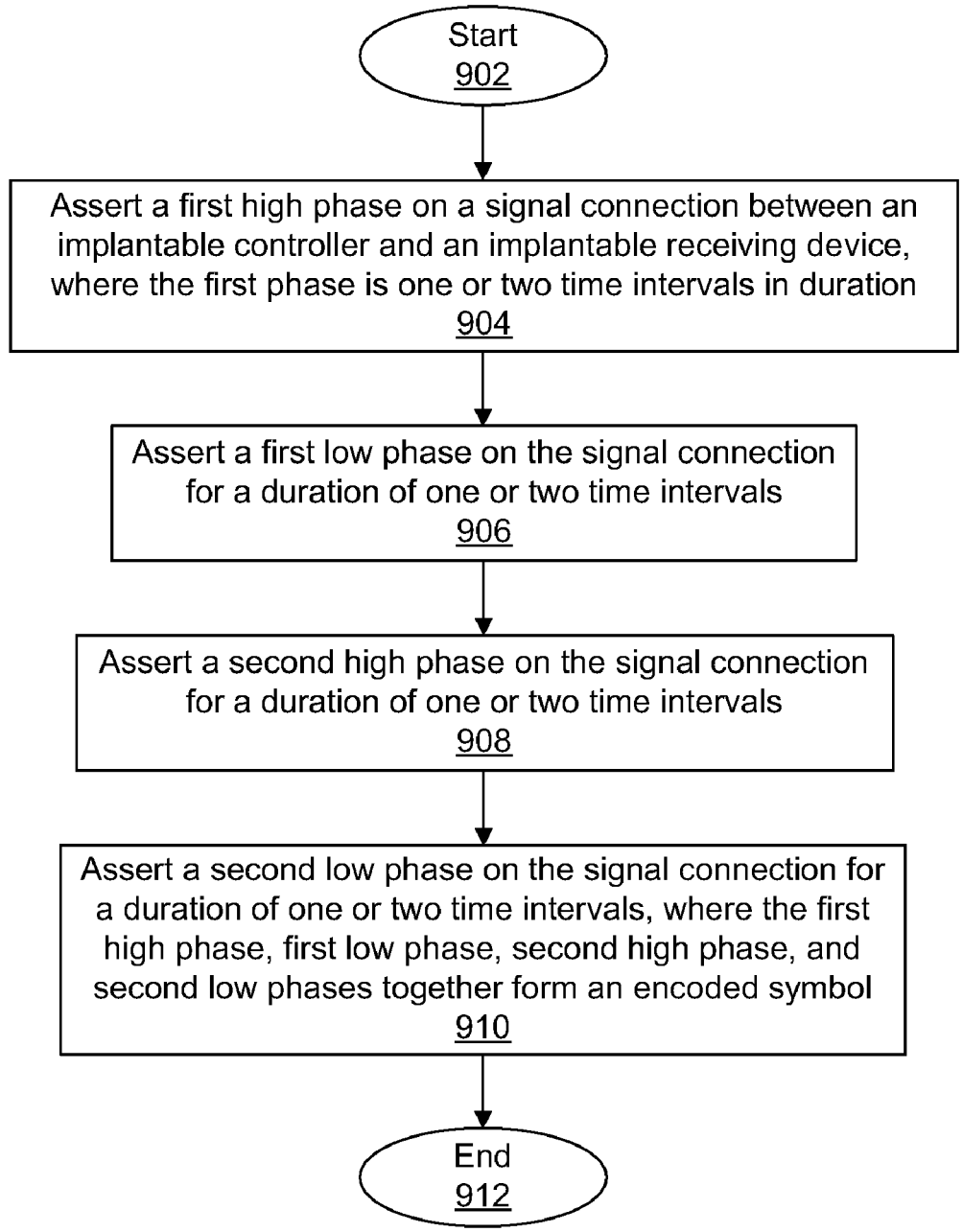
FIG. 9 illustrates a flow diagram for an exemplary method of encoding data for an implantable device in accordance with various aspects of the present invention.

Referring now to FIG. 9, a flow diagram for an exemplary method of encoding data for an implantable device in accordance with various aspects of the present invention is shown. The flow can begin (902), and a first high phase can be asserted on a signal connection between an implantable controller (e.g., an ICD) and an implantable receiving device (e.g., a satellite), where a duration of this first high phase is one or two time intervals (904). For example, this first high phase can represent one of phases 502-A$_1$, 504-A$_1$, 506-A$_1$, or 508-A$_1$, as discussed above. Further, the signal connection may be a single transmission wire that can connect a plurality of satellites to one controller.

Next, a first low phase can be asserted on the signal connection for a duration of one or two time intervals (906). For example, this first low phase can represent one of phases 502-B$_1$, 504-B$_1$, 506-B$_1$, or 508-B$_1$. Then, a second high phase can be asserted on the signal connection for a duration of one or two time intervals (908). For example, this second high phase can represent one of phases 502-A$_2$, 504-A$_2$, 506-A$_2$, or 508-A$_2$. A second low phase can then be asserted on the signal connection for a duration of one or two time intervals (910), and the flow can complete (912). For example, this second high phase can represent one of phases 502-B$_2$, 504-B$_2$, 506-B$_2$, or 508-B$_2$. Further, the first high phase, first low phase, second high phase, and second low phases taken together can form an encoded symbol over six time intervals.

Figure 10:
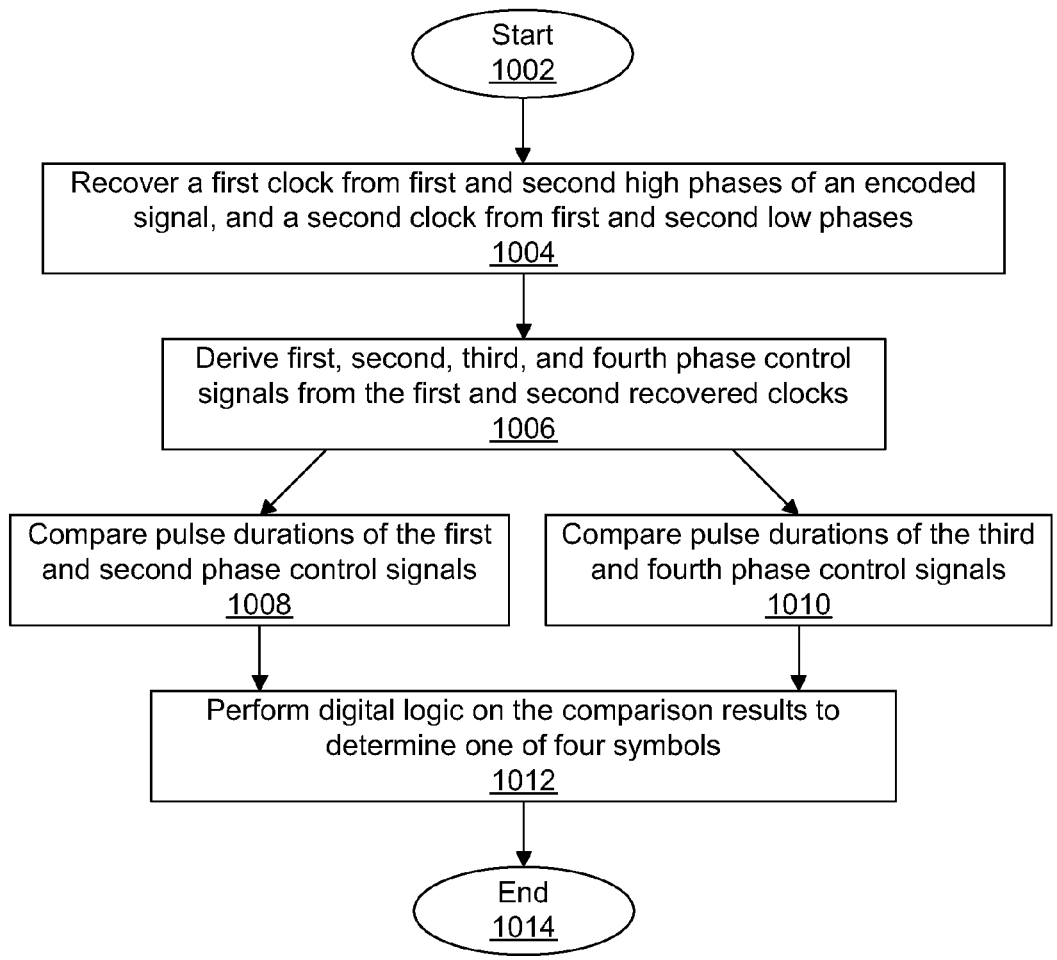
FIG. 10 illustrates a flow diagram for an exemplary method of decoding encoded data in an implantable device in accordance with various aspects of the present invention.

Referring now to FIG. 10, a flow diagram for an exemplary method of decoding encoded data in an implantable device in accordance with various aspects of the present invention is shown. The flow can begin (1002), and a first clock can be recovered from first and second high phases of an encoded signal, while a second clock can be recovered from first and second low phases (1004). For example, such a first clock can be recovered clock 702 corresponding to first high phase 502-A$_1$ and second high phase 502-A$_2$, as shown in FIG. 7. The second clock can be similarly generated, or in some cases may be an inversion of the first clock.

Next, first, second, third, and fourth phase control signals can be derived from the first and second recovered clocks (1006). For example, first and second phase control signals may be $\phi_{A1}$ (waveform 704) and $\phi_{A2}$ (waveform 706), respectively. Third and fourth phase control signals may similarly be derived from the second recovered clock, and may correspond to first and second low phases (e.g., 502-B$_1$ and 502-B$_2$), respectively. Pulse durations can then be compared between the first and second phase control signals (1008) and the third and fourth phase control signals (1010). For example, a DCR circuit portion as shown in FIG. 8 can be utilized for performing this comparison. Then, digital logic can be performed on the comparison results to determine if one of the four encoded symbols (e.g., X, Y, Z, or Start) has been received (1012), and the flow can complete (1014).

Various aspects can allow for area savings in the satellite IC implementation, as compared to other approaches. Utilizing only one signal line for receiving encoded data, as opposed to having two or more lines, such as for data, clock, and other signals, allows for area reduction based on fewer bond pads, and associated circuitry. Also, power savings in various aspects can be about 50%, or as high as about 70%, about 90%, and even as high as about 98% in some cases, when compared against a three-wire approach with full swing transitions, as opposed to one wire with small swing (e.g., about 500 mV) transitions, and at the same transmission frequency.

Implantable Bidirectional Communicators

Implantable devices suitable for biomedical applications must meet low power and small area requirements. For controllers that are located remotely from other devices (i.e., satellite devices), such as in a pacemaker application, communication to and from the satellite devices should be "minimalistic" in terms of both the physical interface structure, and the operation thereof. Such interfaces and protocols supporting bidirectional communication for implantable devices should have a reduced width physical bus interface, and a simplified encoding scheme that requires very little power for operation.

An interface for communicating from an implantable cardio-defibrillator (ICD) controller circuit to an IC located in a vascular lead electrode satellite employs defined symbols to accommodate data and/or command conveyance. The symbols are typically encoded in the ICD, transmitted via interconnecting wires to a satellite, and then decoded within the satellite device in order to ascertain the particular communicated bits of information, and thus any associated data or commands.

One such command that can be conveyed (e.g., using a predetermined combination of symbols) by a controller to a satellite device is a request for "talkback" for return communication of electrode configuration and/or status of the satellite device. Thus, a talkback mode or period works with the satellite device communicating its own configuration information back to the controller or ICD. Such a talkback interface/mode for implantable bidirectional communicators and/or devices is described herein in terms of: (i) system arrangements and circuitry showing example circuit structures in both the controller and the satellite IC; (ii) talkback interface waveforms showing operations for the requesting and returning of information via the satellite IC; and (iii) methods of bidirectional communication via an implantable device.

In order to reduce overall system size and complexity to effectively implement implantable devices configured for bidirectional communication, a simplified data encoding and talkback interface having one signal for data encoding and another signal for a common ground connection can be used. Because no separate clock signal is utilized over this interface, and because no separate reference signal need be used for data recovery or demodulation, such an interface approach may be referred to as "self-clocking" and "self-referencing." Using this approach, the encoding of data signals for transmission from/to remote devices can substantially reduce the size and complexity of the system relative to directly transmitted data approaches.

A form of phase shift keying (PSK) is one method to provide a self-referencing and self-clocking interface approach in data encoding for transmission from the controller to the satellite IC. Other approaches, including amplitude shift keying (ASK), or other suitable forms of modulation, may also be used to encode data in various aspects, and in some cases can be used in conjunction with PSK-like approaches. Various aspects can utilize ASK modulation for talkback or return communication from the satellite IC to the controller. Four symbols are used for communicating from an ICD circuit to an IC located in a vascular lead electrode satellite, which may be in a multi-electrode lead (MEL) coupled to the ICD. In return, a string of logical '1' and '0' bits can be communicated during a talkback mode from the satellite IC to the controller in a predetermined order to convey a particular configuration (e.g., an electrode configuration) or state of the satellite IC.

A single wire plus a ground connection can be used for data encoding in communication from an ICD to a satellite, as well as for return communication from the satellite to the ICD in a talkback mode. Further, such ground connections may be coupled via a terminal to a human body. The single wire can be used to transmit encoded clock and data information (e.g., logical '1' and '0' bit values). Thus, no separate clock signal need be transmitted to or from any of the satellite ICs. For demodulation, a data clock recovery (DCR) circuit can be utilized in the satellite, and a talkback bit sensing circuit can be used in the ICD/controller, to derive communicated symbols or data/status bits without the aid of a separately-supplied clock signal. In one particular example, encoded symbols are conveyed from over a time period of six time intervals, while bits of data conveyed during talkback can each span a time period of eight time intervals.

Other numbers of time intervals can be used in various aspects. Here, a simplified and robust implementation can generally include a same "1010" pattern for both symbol transmission and talkback data/status bit transmission. For data encoded for transmission from the controller to a satellite, each high or low phase is maintained for approximately one or two time intervals. However, for data bits transmitted from the satellite to the controller, each high or low phase may be maintained for two time intervals. This can allow for symbol patterns and data/status bits in the transmitted signals to be driven from a same clock source or other reference point, resulting in further simplification.

For example, a time interval is about 0.5 μs (500 ns), thus two time intervals can have a total duration of about 1 μs (1,000 ns). Any suitable time interval and/or pulse or signal state durations can be accommodated in various aspects. For example, time intervals can be in a range of from about 200 ns to 800 ns, such as from about 250 ns to 750 ns, and including from about 400 ns to 600 ns. As technology improves, the time intervals can even decrease by orders of magnitude (e.g., into the tens of nanoseconds, or less, range).

Figure 11:
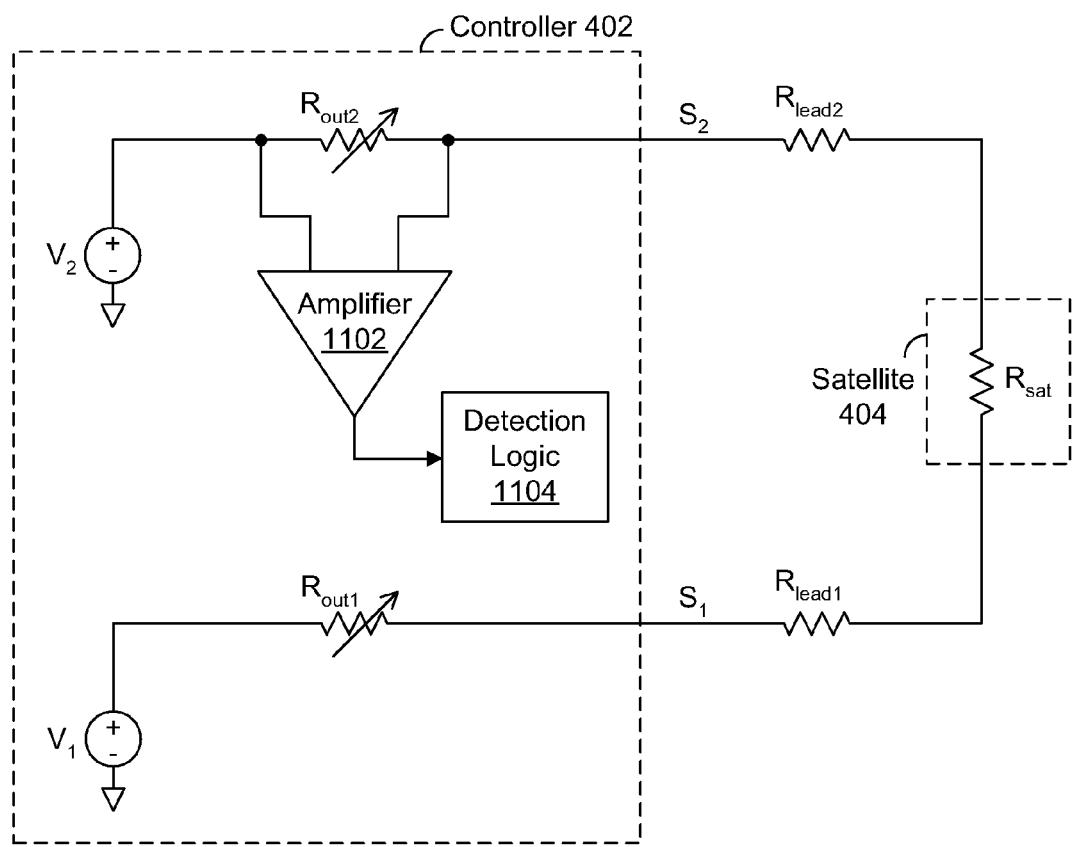
FIG. 11 illustrates an exemplary simplified talkback bit sensing circuit portion in accordance with various aspects of the present invention.

FIG. 11 shows an exemplary simplified talkback bit sensing circuit portion in accordance with various aspects of the present invention. Controller 402 can be coupled to satellite 404 via lead lines $S_1$ and $S_2$ (see, e.g., FIG. 4) having resistances $R_{lead1}$ and $R_{lead2}$, respectively. Such resistances can vary depending upon the materials used to form the lead lines, temperatures, and lengths of the lead lines. For example, resistances $R_{lead1}$ and/or $R_{lead2}$ may suitably be any value in a range of from about 1Ω to 7.5Ω, such as from about 2Ω to 6Ω, including from about 3Ω to 5Ω, and more specifically about 4Ω.

Also, and as will be discussed in more detail below, voltage sources $V_1$ and $V_2$ can vary or swing from about 0 V to about 0.5 V (500 mV), and from about 4.5 V to about 5 V, respectively, during symbol transmission from controller 402. However, any suitable voltage levels can be utilized for $V_1$ and/or $V_2$ for such transmission. For example, various aspects can utilize voltages for supply $V_1$ with "rails" having absolute values in a range of from about 150 mV to 850 mV, such as from about 250 mV to 750 mV, and including from about 400 mV to 600 mV. Further, various aspects can utilize voltages for supply $V_2$ with rails having absolute values in a range of from about 1.5 V to 8 V, such as from about 1.8 V to 7.5 V, including from about 2.5 V to 6.5 V, more specifically from about 3.3 V to 6V, and most specifically about 5 V.

Resistances $R_{out1}$ and $R_{out2}$ can be variable controller output impedances that may change between a low impedance state to a high impedance state. In various aspects, the high impedance state is entered periodically when in talkback mode, and this is when amplifier 1102 is configured to sample a voltage difference across its input terminals. Detection logic 1104 may then receive an amplified output signal from amplifier 1102, and thus derive configuration/state of the selected satellite 404. Resistance $R_{sat}$ can represent an impedance of the satellites as seen on lead lines $S_1$ and $S_2$. In a low impedance state, resistances $R_{out1}$ and/or $R_{out2}$ can suitably be, for example, any value in a range of from about 2.5Ω to 25Ω, such as from about 5Ω to 15Ω, including from about 7.5Ω to 12.5Ω, and more specifically about 10Ω. In a high impedance state, resistances $R_{out1}$ and/or $R_{out2}$ can be increased and may suitably be, for example, any value in a range of from about 100Ω to 500Ω, such as from about 150Ω to 400Ω, and including from about 250Ω to 350Ω, and more specifically about 300Ω.

When in the talkback mode, resistance $R_{sat}$, representing a selected satellite 404, can be altered to effectively communicate a bit '0' or '1' state from the satellite to controller 402. In this fashion, a relatively low resistance (e.g., $R_{sat}$ of about 200Ω) can produce a relatively high voltage difference across resister $R_{out2}$ in controller 402. Similarly, a relatively high resistance (e.g., $R_{sat}$ of about 2 KΩ) can produce a relatively low voltage difference across resister $R_{out2}$ in controller 402. It is this voltage difference that can be amplified using amplifier 1102. As will be discussed in more detail below, a time interval in which such a relatively high voltage difference across resister $R_{out2}$ is amplified can determine a communicated bit state (e.g., '0' or '1') from satellite 404 to controller 402.

In a relatively low resistance state, resistance $R_{sat}$ may suitably be, for example, any value in a range of from about 50Ω to 500Ω, such as from about 100Ω to 350Ω, including from about 150Ω to 250Ω, and more specifically about 200Ω. In a relatively high resistance state, resistance $R_{sat}$ may suitably be, for example, any value in a range of from about 1 KΩ to 3.5 KΩ, such as from about 1.5 KΩ to 3 KΩ, including from about 1.75 KΩ to 2.5 KΩ, and more specifically about 2 KΩ. Further, a ratio of a relatively high value of resistance $R_{sat}$ to a relatively low value of resistance $R_{sat}$ can be about 10:1. Other ratios (e.g., in a range of ratios from about 5:1 to about 15:1, such as from about 7:1 to 12:1, and including from about 8.5:1 to 11.5:1) can be utilized in various aspects, as particular design constraints and margins will allow.

An alternative approach to using a variable resistor (e.g., $R_{out2}$) coupled to a differential amplifier (e.g., 1102) to sense a pull-down via satellite 404 (e.g., an $R_{sat}$ value of about 200Ω) is to use two matched capacitors and a comparator. In this approach, one capacitor may be charged in relation to an $R_{sat}$ value of about 200Ω (relatively high current), and another capacitor can be charged in relation to an $R_{sat}$ value of about 2 KΩ (relatively low current). In this fashion, the capacitor corresponding to an $R_{sat}$ value of about 200Ω will charge to a higher voltage level in the same time period, resulting in a corresponding comparison result that can be mapped to a communicated bit state.

Generally, a voltage difference of about 200 mV may be developed across resister $R_{out2}$ during sensing. However, any suitable voltage difference based on sensing margins and circuit implementations can be accommodated in various aspects. For example, any value in a range of from about 10 mV to 500 mV, such as from about 25 mV to 350 mV, and including from about 100 mV to 250 mV, can be utilized. In addition, detection logic 1104 can include logic circuitry to detect possible error states in signal transmission, and to provide an associated indication and/or default detected data bit substitution value in response.

Figure 12:
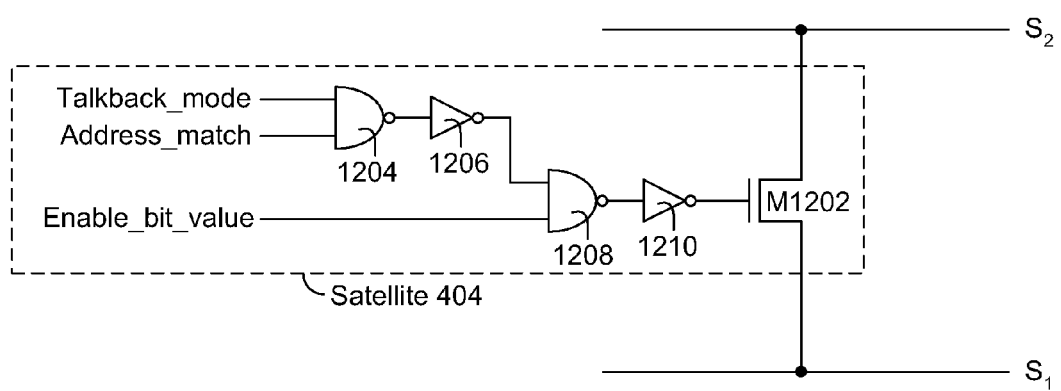
FIG. 12 illustrates a first exemplary talkback communication circuit portion in a satellite IC in accordance with various aspects of the present invention.

In order to adjust between the relatively high and relatively low resistances of $R_{sat}$ in a talkback mode, a controllable transistor may be placed in the satellite device IC between lead lines $S_1$ and $S_2$. Referring now to FIG. 12, a first exemplary talkback communication circuit portion in a satellite IC in accordance with various aspects of the present invention is shown. NMOS transistor M1202 can be controlled using combinational logic (e.g., NAND gates 1204 and 1208, as well as inverters 1206 and 1210). Other types of logic gates (e.g., NOR gates, exclusive-OR/NOR gates, as well as dynamic gates, such as pre-charged logic, and small-signal swing circuitry), as well as sample-and-hold circuitry, and/or other control signals can also be used in various aspects. Further, other types of transistors (e.g., bipolar transistors, or PMOS type MOS transistors), or other types of switching devices, can be utilized in place of NMOS transistor M1202.

In various aspects, control signals can include a talkback mode enable (e.g., talkback_mode), an address match indication (e.g., address_match), and an indication of the particular bit value for communication (e.g., enable_bit_value). In operation, a logical high level can be presented at one input of NAND gate 1208 when an address sent by controller 402 matches that of satellite 404 while in talkback mode. The bit value can be conveyed by a high pulse of enable_bit_value during a predetermined time interval to turn on transistor M1202. For example, during talkback mode, enable_bit_value may be high during a first or a second low phase of a predetermined "1010" signal pattern for transmission from satellite 404 to controller 402. For satellite devices that are not selected (e.g., address_match is low), transistor M1202 remains off, resulting in a high impedance contribution therefrom across lead lines $S_1$ and $S_2$.

Figure 13:
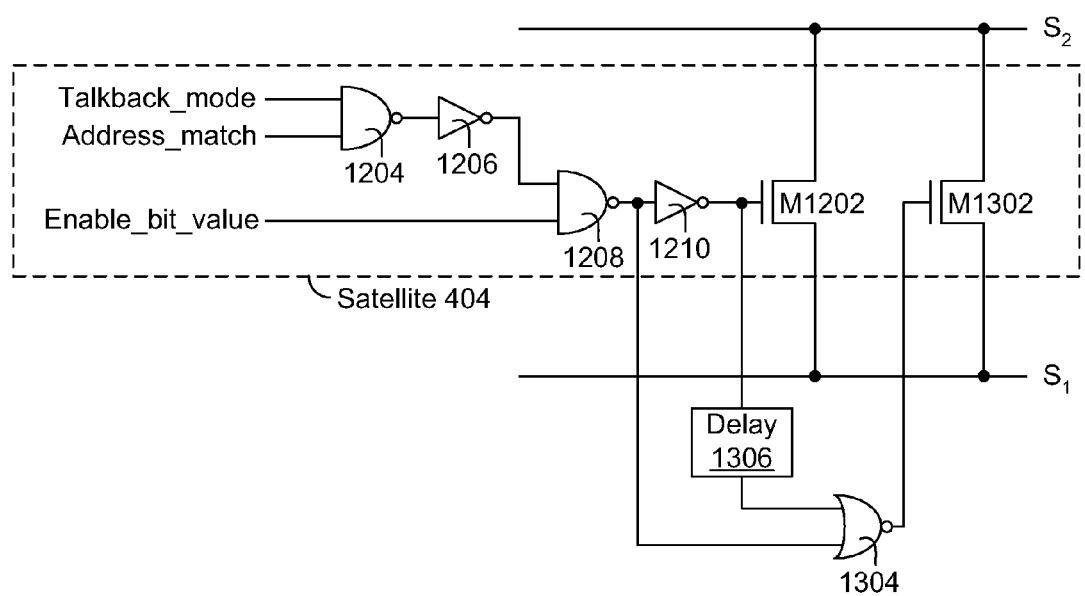
FIG. 13 illustrates a second exemplary talkback communication circuit portion in a satellite IC in accordance with various aspects of the present invention.

Referring now to FIG. 13, a second exemplary talkback communication circuit portion in a satellite IC in accordance with various aspects of the present invention is shown. For this example circuit portion, a pre-emphasis can be controlled by pulling lead lines $S_1$ and $S_2$ together when talkback mode is initially enabled by using NMOS transistor M1302 (e.g., in parallel with NMOS transistor M1202). Combinational and/or timing control logic (e.g., NOR gate 1304 and delay circuit 1306). Other types of logic gates (e.g., NAND gates, exclusive-OR/NOR gates, as well as dynamic gates, such as pre-charged logic, and small-signal swing circuitry), as well as sample-and-hold circuitry, and/or other control signals can also be used in various aspects. Further, other types of transistors (e.g., bipolar transistors, or PMOS type MOS transistors), or other types of switching devices, can be utilized in place of NMOS transistor M1302. In addition, any suitable type of delay circuit (e.g., inverters, resistor, and/or capacitor networks) can be used for delay circuit 1306.

In various aspects, a talkback enable signal at the gate of NMOS transistor M1202 can be fed into delay circuit 1306. Also, an inverted version of this talkback enable signal can be taken from the output of NAND gate 1208. In operation, a logical low level can be presented at each input of NOR gate 1304 when talkback mode is initially enabled. This state may last until delay circuit 1306 times out, thus turning NMOS transistor M1302 off. In this fashion, NMOS transistor M1302 is turned on when talkback mode is enabled, for a duration of the delay from delay circuit 1306. Further, delay circuit 1306 can have a user programmable delay such that an optimized time for the pre-emphasis from NMOS transistor M1302 on lead lines $S_1$ and $S_2$ can be determined.

Interface Waveforms for Implantable Bidirectional Communicators

Operation of the present bidirectional communication interface for implantable devices is shown using various example waveforms that illustrate a data encoding interface operation, and a talkback interface from a satellite device to a controller operation in various aspects. These example waveforms show example data encoding in the form of communicated symbols from a controller to a satellite IC device (see, e.g., FIG. 5), and also talkback or return communication from a selected satellite IC device to the controller (see, e.g., FIGS. 14-15).

As discussed above with reference to FIG. 5, data can be decoded or recovered in a satellite device, where symbols may be identified in relation to the Start symbol (e.g., such symbols may follow a Start symbol). Table 1 above also shows one example of binary coded data relative to symbol pairs. Such binary coded data can be used in addressing one of eight satellite devices. For example, if N=7 in FIG. 4 (so 8 satellite devices on a particular lead or MEL), symbol pair YZ can be utilized in addressing to select satellite 404-1, and symbol pair ZZ can be used in addressing for selection of satellite 404-N. Of course, additional symbols strung together can allow for longer binary strings, and expansion of the table shown. Further, other symbol definitions, and corresponding binary data bit values can also be accommodated in various aspects.

Other approaches to data encoding suitable for implantable devices can include where each signal phase defines a particular bit position, and each subsequent phase has a duration of half that of the previous phase. However, such an approach typically requires comparison to a known reference or group of references, which can be a relatively difficult implementation. In self-referencing approaches of various aspects, values or phases can simply be compared against each other. Thus, no separate reference may be needed, and the overall circuit complexity can be substantially reduced.

Figure 14:
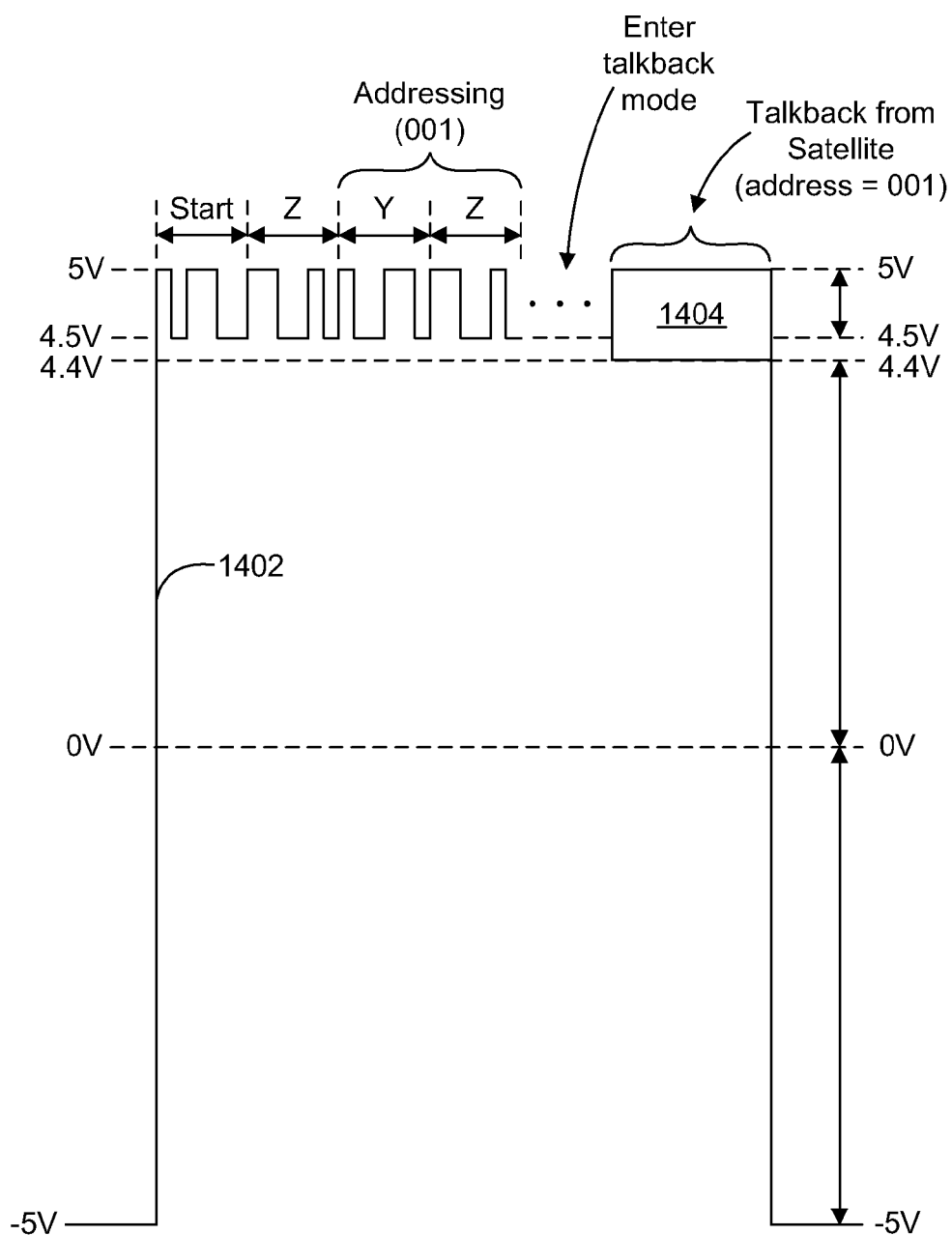
FIG. 14 illustrates a full-swing waveform for enabling talkback mode in accordance with various aspects of the present invention.

FIG. 14 shows a full-swing waveform for enabling talkback mode in accordance with various aspects of the present invention. Waveform 1402 can be driven by either an ICD (where received by a satellite IC), or by a selected satellite IC (where received by the ICD/controller). In various aspects, encoded data symbols (e.g., symbols Start, Y, and Z), as well as communication during talkback period 1404, can be accomplished using a relatively small swing voltage variation over a larger voltage level. For example, waveform 1402 can range from about −5 V to about 4.5 V, and then between about 4.5 V and about 5 V to support data encoding from the controller to the satellite. Accordingly, a "low phase" as discussed above with reference to FIG. 5 can be about 4.5 V, while a "high phase" may be about 5 V, as shown in the particular example of FIG. 14. However, the talkback period 1404 can involve a voltage range from about 100 mV below an amplitude of about 4.5 V, thus more specifically from about 4.4 V to about 5 V for return data bit communication.

In this fashion, a satellite configuration in the form of a series of bits can be sent from a selected satellite device to a controller during a talkback mode. In various aspects, talkback mode can be entered by the controller sending a series of symbols along lead lines $S_1/S_2$. For example, a 'Start' symbol, followed by a 'Z' symbol, and then followed by satellite device addressing can result in the selected satellite device entering talkback mode. In this particular example, symbol pair 'YZ' designating an address of '001' (see, e.g., Table 1), can be used to select satellite device 404-1, as shown above in FIG. 4. Accordingly, satellite device 404-1 having an address of '001' can provide its electrode configuration and/or status by sending a series of bits during talkback period 1404.

As discussed above, a differential amplifier 1102 can be utilized to essentially compare a voltage amplitude of a low signal phase (e.g., about 4.4 V) versus a predetermined level (e.g., about 4.5 V). For example, this is done by turning on transistor M1202 (and possibly transistor M1302 as well for pre-emphasis) to partially discharge lead line $S_2$, and thus to create a voltage differential across resistor $R_{out2}$ (e.g., by increasing the loop current). Accordingly, no separate reference voltage may be required in order to sense the data bit communicated from the selected satellite device (e.g., 404-1) to the controller (e.g., 402). Further, while the pull-down voltage portion may be about 100 mV (e.g., the difference between about 4.5 V and about 4.4 V), this voltage difference may suitably be, for example, any value in a range of from about 50 mV to 500 mV, such as from about 70 mV to 400 mV, and including from about 85 mV to 300 mV, with the high end of this range forming a possible design trade-off with circuit current limitations (e.g., through the circuit portion shown in FIG. 11).

The negative portion of waveform 1402 can allow for charge balancing on this interface signal or lead line. Thus, a negative portion of the signal can offset the positive portion by remaining at or near a negative rail (e.g., about −5 V) for approximately a same amount of time as the signal is at or near a positive rail (e.g., in the range from about 4.5 V to about 5 V). In this fashion, charge balance can be achieved on the signal interfacing between the ICD and one or more satellite devices in an MEL. As an alternative signaling configuration, an $S_2$ lead line may be held at a level of about 5 V, while the $S_1$ lead line varies from about 0 V to about 500 mV in order to convey signals (e.g., symbols and talkback bits). Amplitude modulation during the talkback period for such a configuration may then range to about 600 mV, or about 100 mV over a nominal high phase voltage level of about 500 mV. Thus, various aspects can accommodate signaling via a voltage difference between lead lines $S_1$ and $S_2$, as opposed to considering merely an absolute level of either lead line.

Figure 15:
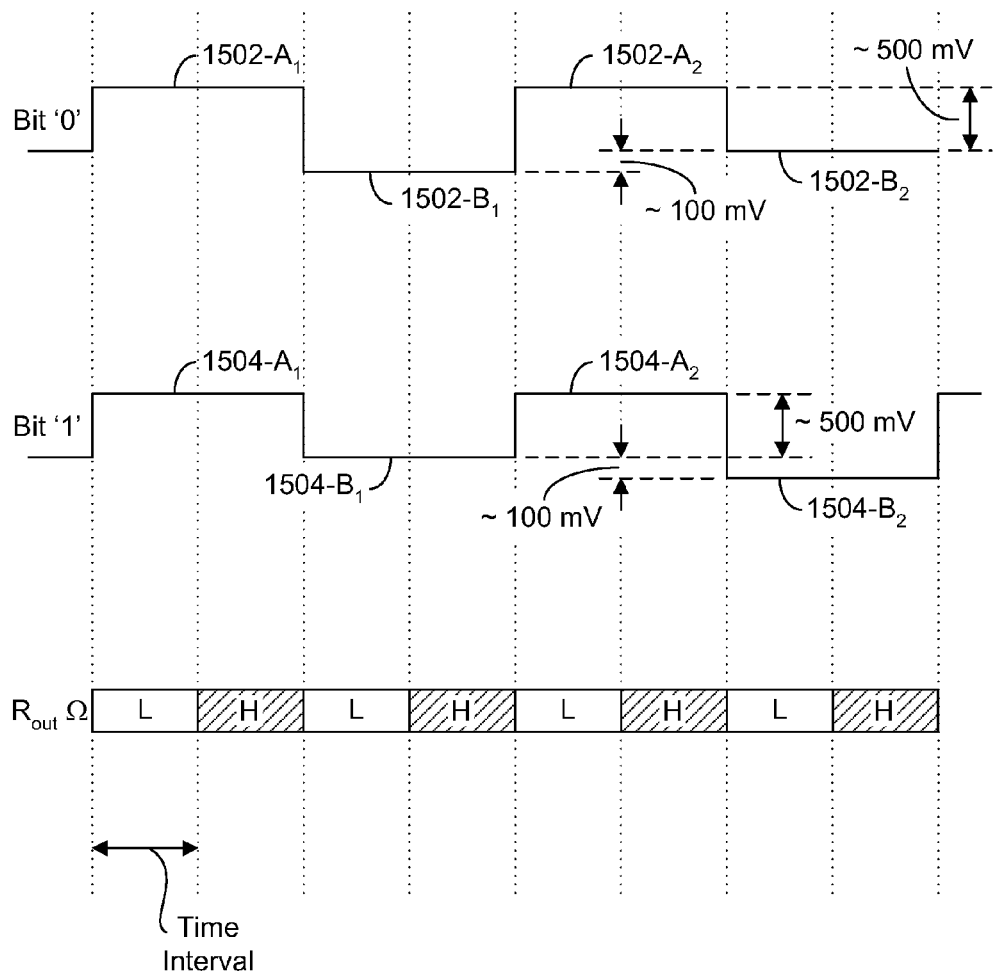
FIG. 15 illustrates exemplary talkback data bit waveforms in accordance with various aspects of the present invention.

FIG. 15 shows exemplary talkback data bit waveforms in accordance with various aspects of the present invention. Such waveforms can represent encoded data bits transmitted from a selected satellite device to the controller. A logic '0' data bit can be encoded in a signal pattern having a first high phase 1502-$A_1$ lasting for two time intervals, then a first low phase 1502-$B_1$ lasting for two time intervals, then a second high phase 1502-$A_2$ lasting for two time intervals, followed by a second low phase 1502-$B_2$ also lasting for two time intervals, for a total of eight time intervals. Further, first low phase 1502-$B_1$ can have an amplitude less than that of second low phase 1502-$B_2$ by about 100 mV, where nominal high-to-low phase amplitude differences are about 500 mV, as shown. Thus, a talkback data bit '0' can be derived in the controller by sensing a voltage differential during or corresponding to predetermined phases (e.g., low phases), as shown below in Equation 5.

$$\text{Talkback Bit '0'}: B_1(V) < B_2(V) \tag{5}$$

Similarly, a different waveform pattern can represent an encoded version of a data bit '1' for transmission from a selected satellite device to the controller. A logic '1' data bit can be encoded in a signal pattern having a first high phase 1504-$A_1$ lasting for two time intervals, then a first low phase 1504-$B_1$ lasting for two time intervals, then a second high phase 1504-$A_2$ lasting for two time intervals, followed by a second low phase 1504-$B_2$ also lasting for two time intervals, for a total of eight time intervals. Further, second low phase 1504-B$_2$ can have an amplitude less than that of first low phase 1504-B$_1$ by about 100 mV, where nominal high-to-low phase amplitude differences are about 500 mV, as shown. Thus, a talkback data bit '1' can be derived in the controller by sensing a voltage differential during or corresponding to predetermined phases (e.g., low phases), as shown below in Equation 6.

Talkback Bit '1':$B_1(V)$>$B_2(V)$ (6)

As noted above, while a nominal amplitude difference during transmission may be about 500 mV, and an additional amplitude difference for talkback data bit communication may be about 100 mV, other suitable values can also be used in various aspects. For example, nominal amplitude differences can include values in a range of from about 150 mV to about 850 mV, such as from about 250 mV to about 750 mV, and including from about 400 mV to about 600 mV. Further, the additional amplitude difference for talkback communication (i.e., the pull-down voltage portion) may suitably be, for example, any value in a range of from about 50 mV to about 500 mV, such as from about 70 mV to about 400 mV, and including from about 85 mV to about 300 mV. In addition, other types of modulation or amplitude comparison can be accommodated in various aspects. For example, amplitude comparisons between signal high phases (e.g., 1504-A$_1$ versus 1504-A$_2$) can allow for alternative or additional data bit communication during talkback mode.

In various aspects, some time intervals in talkback mode can be designated for amplitude sensing. These designated time intervals can correspond to variable controller output impedances (e.g., R$_{out2}$) being put in the high impedance (e.g., about 300Ω) state. This can be controlled by using a clock that is internal to the controller (and that is not transmitted over the S$_1$/S$_2$ interface), and that corresponds to alternating time periods. This is shown in FIG. 15 as "H" for high impedance amplitude sensing time periods, while other portions are labeled "L" corresponding to R$_{out2}$ being put in a low impedance (e.g., about 10Ω) state. Such predetermined time period controls can mitigate pull-down device M1202 discharging lead line S$_2$ so much that it is difficult to return to its previous value. Thus, transistor M1202 may be pulsed on for durations of about one time interval (e.g., about 500 ns) during talkback mode.

In various aspects, two types of information can be conveyed to the controller (e.g., 402) during talkback about each electrode (e.g., e0, e1, e2, and e3) in a satellite device: (i) enable; and (ii) polarity. This information can convey status and/or configuration of the selected satellite device. Further, other data, defined symbols, etc., can also be accommodated during talkback mode in various aspects. Table 2 below shows an example mapping of enable and polarity parameters for each electrode.

TABLE 2

| Electrode | e0 | e1 | e2 | e3 |
|---|---|---|---|---|
| Enable | e0c | e1c | e2c | e3c |
| Polarity | p0c | p1c | p2c | p3c |

Thus, a full configuration of a satellite device during talkback can be conveyed as an 8-bit string, with each bit position in the string corresponding to a particular configuration parameter. For example, the data in Table 2 may be conveyed in an order e0c, p0c, e1c, p1c, e2c, p2c, e3c, and p3c. Table 3 below shows example switch matrix connections and meanings for each data bit in the conveyed bit string during talkback.

TABLE 3

| Parameter | Value | Defined Meaning |
|---|---|---|
| eXc | 1 | Enable |
| eXc | 0 | Disable |
| pXc | 1 | Electrode connected to S$_2$ |
| pXc | 0 | Electrode connected to S$_1$ |

Thus, following the example above, if a bit string of '00101000' is communicated from the selected satellite device to the controller, the derived configuration of that satellite device would be electrodes e0 and e3 disabled, electrodes e1 and e2 enabled, with each enabled electrode connected to lead line S$_1$. Also, while a bit string of 8-bits in length may be provided by a satellite device during talkback mode, other numbers of bits, as well as other orders of the bits, may also be provided in various aspects. For example, an encoded version of the configuration can be provided, as well as additional bits for other types of configuration information.

Various aspects can also withstand substantial voltage level degradation over time due to relatively small signal swings of about 500 mV (above or below the corresponding supply or reference level), as compared to typical supply voltages of about 5 V. Further, such supply voltages may also be programmable, in addition to resistors in the talkback bit sensing circuit portion of FIG. 11, and transistors M1202 and/or M1302 (e.g., to adjust transistor width). For example, metal layer options, register-based controls, laser fuses, etc., can be used for adjusting these values as part of the characterization process. In particular, adjustments may be made to resistors R$_{out1}$ and R$_{out2}$, as well as transistors M1202 and/or M1302, as may be necessary to improve sensing or other operating margins.

Implantable Device Bidirectional Communication Methods

Using the simplified data encoding and talkback interfaces of the present implantable bidirectional communication devices, methods of entering a talkback mode by sending appropriate commands and addressing from a controller device to a satellite IC device, whereby the selected satellite device can then reply with configuration information back to the controller, will now be discussed. Using these methods along with the circuitry and interface described herein can support a simplified and robust bidirectional communication approach suitable for implantable devices.

Figure 16:
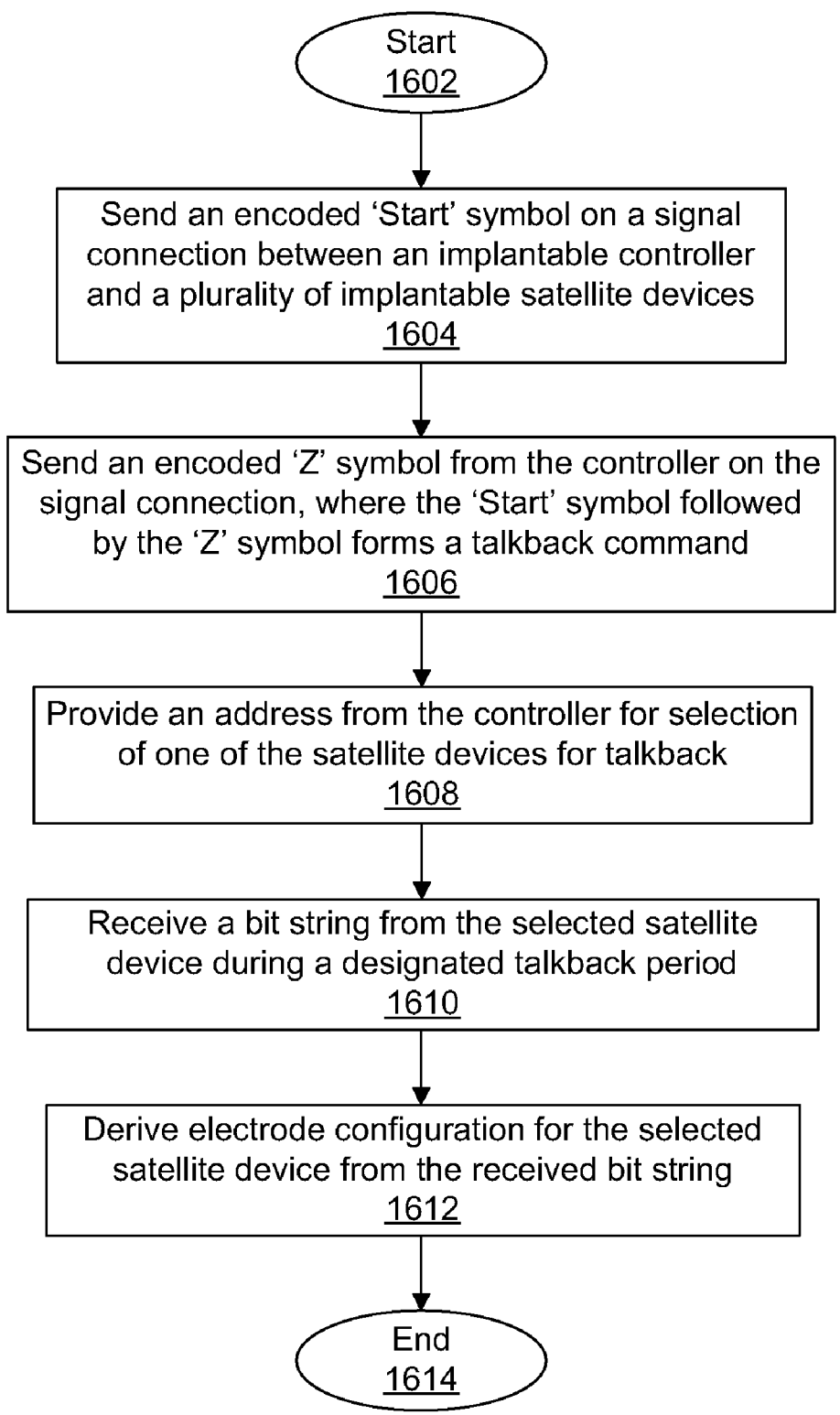
FIG. 16 illustrates a flow diagram for an exemplary method of operating a talkback mode in accordance with various aspects of the present invention.

FIG. 16 shows a flow diagram for an exemplary method of operating a talkback mode in accordance with various aspects of the present invention. The flow can begin (1602), and an encoded symbol (e.g., a 'Start' symbol) can be sent by an implantable controller (e.g., an ICD) on a signal connection between the controller any number of implantable receiving satellite devices (1604). The signal connection may be a single transmission wire that can connect a plurality of satellites to one controller. Next, another symbol (e.g., a 'Z' symbol) can be sent from the controller on the signal connection that connects the plurality of satellites (1606). Together, these encoded symbols can form a command to enter talkback mode. Alternatively, a single symbol, or any other combination of symbols or control bits, may form or otherwise indicate a talkback command.

Along with a talkback command initiation, addressing is provided by the controller to indicate which of the satellites is to be accessed for talkback (1608). In various aspects, this addressing may include transmission of two sequential symbols, with corresponding binary coded data, as shown above in Table 1. Once the selected satellite device has entered talkback mode, a bit string can be received from that device (1610). As discussed above, this bit string can convey electrode configuration information from the selected satellite device. Thus, this electrode configuration can be derived in the controller using sensing circuitry (1612), such as shown above in FIG. 11, completing the flow (1614).

Figure 17:
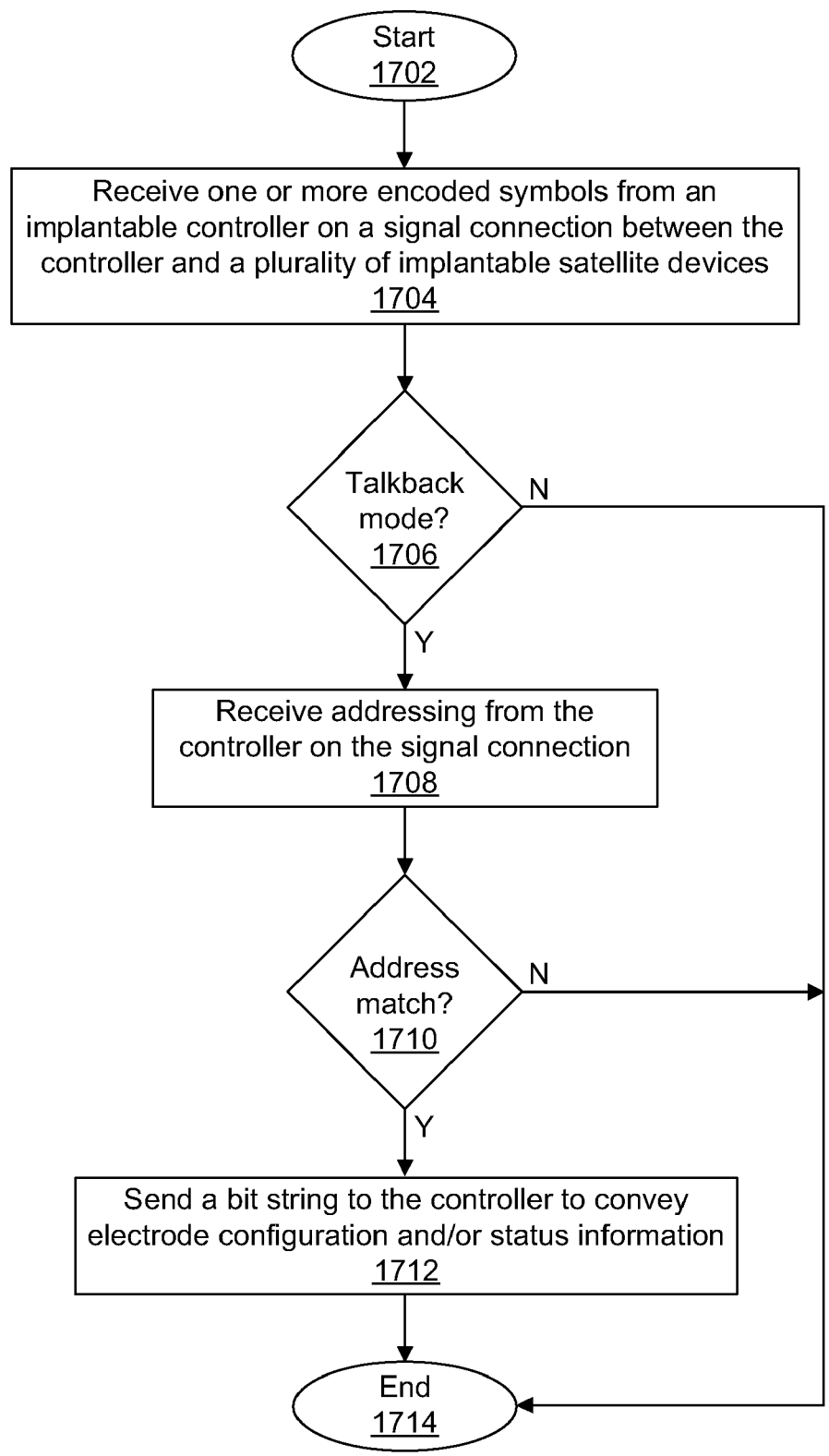
FIG. 17 illustrates a flow diagram for an exemplary method of communicating configuration information from an implantable satellite IC in accordance with various aspects of the present invention.

FIG. 17 shows a flow diagram for an exemplary method of communicating configuration information from an implantable satellite IC in accordance with various aspects of the present invention. The flow can begin (1702), and one or more encoded symbols can be received from a controller on a signal connection between the controller and satellite devices (1704). As discussed above, one or more symbols (e.g., a 'Start' symbol followed by a 'Z' symbol), or any other suitable command for entering a talkback mode can be received in a satellite device. In various aspects, each satellite device can contain command registers and comparison circuitry for determining whether a current symbol or sequence of symbol forms a particular command (e.g., to enter talkback mode).

If a satellite device detects such a command as a talkback mode initiation (1706), addressing can be received from the controller on the signal connection (1708). For example, such addressing can include two sequential symbols (e.g., as shown in Table 1) to select a particular satellite device. In various aspects, each satellite device can contain address registers and comparison circuitry for determining whether received address information matches an assigned address for a particular device (e.g., '001' for satellite 404-1). If a satellite device has determined that it is in talkback mode (1706) and that it is the device selected for talkback participation (1710), this selected device can send a bit string to the controller to convey its electrode and/or status information (1712), completing the flow (1714).

Sleep and Wakeup Control and Circuitry

In various aspects, the communication scheme is implemented such that a lead configuration is established using a series of commands. The communication includes a bi-polar signal, which two advantages in this implementation: (i) an improvement in electrode charge balance; and (ii) resistance to tissue capture. In various aspects, the satellite IC (e.g., 404) uses a "sleep" command that disables the DCR circuitry (e.g., as shown in FIG. 8) so that the satellite IC does not draw power during a pacing pulse. While the satellite IC device is in a sleep mode, any commands provided to the device may be ignored. To come out of the sleep mode and accept commands, a "wakeup" function may be utilized to enable communication between controller 402 and satellite device 404.

Figure 18:
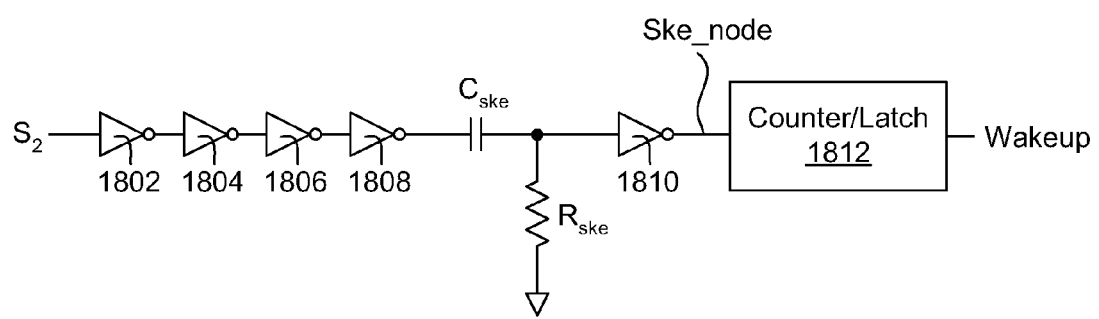
FIG. 18 illustrates a wakeup control signal generation circuit in accordance with various aspects of the present invention.

FIG. 18 shows a wakeup control signal generation circuit in accordance with various aspects of the present invention. One of the lead lines (e.g., $S_2$) can be input to a string of buffers or inverters, 1802, 1804, 1806, and 1808. The output of inverter 1808 can then be input to an RC circuit (e.g., $R_{ske}$ and $C_{ske}$) that provides an input to inverter 1810. For example, resistance $R_{ske}$ may suitably be any value in a range of from about 1 KΩ to 5 KΩ, such as from about 1.5 KΩ to 3 KΩ, and more specifically about 2 KΩ. Capacitance $C_{ske}$ may suitably be, for example, any value in a range of from about 0.2 pF to about 3 pF, such as from about 0.5 pF to about 1.5 pF, and more specifically about 1 pF. Counter/latch circuit 1812 can receive an output from inverter 1810 (e.g., Ske_node), and provide a wakeup control signal therefrom. The wakeup signal is generated by essentially counting a number of pulses (e.g., 4 cycles following the first cycle at a nominal 1 MHz rate) on lead line $S_2$, where a high portion of the first such pulse may be about twice as wide as that of the other high pulses.

Figure 19:
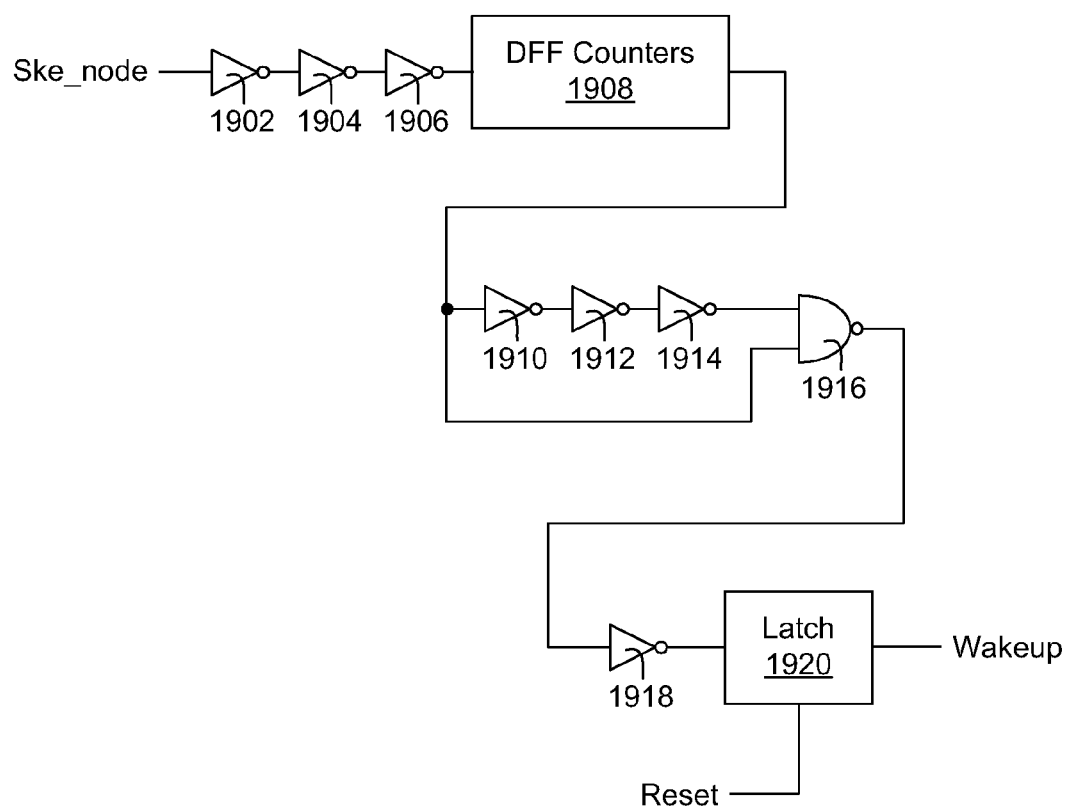
FIG. 19 illustrates a counter and latch control for the wakeup control signal generation circuit in accordance with various aspects of the present invention.

FIG. 19 illustrates a counter and latch control for the wakeup control signal generation circuit in accordance with various aspects of the present invention. Signal Ske_node is fed into an odd number of inversion stages (e.g., inverters 1902, 1904, and 1906), an output of which is provided to DFF counters 1908. For example, three D-type flip-flop (DFF) counter stages can be used to allow for counting of up to 8 cycles in DFF counters 1908. Of course, any suitable type of flip-flop or counting structure can be utilized. Also, any predetermined number of pulses on lead line $S_2$ can be counted prior to enabling the wakeup mode.

Once a particular count on lead line $S_2$ is attained, the output of DFF counters 1908 goes high. This high transition input to inverter 1910 and NAND gate 1916 causes a low-going pulse to fire at the output of NAND gate 1916. This is accomplished using the inverting delay of inverters 1910, 1912, and 1914. Of course, any suitable pulse generation circuit can be utilized. The low-going pulse may be converted into a high-going pulse by inverter 1918. This high-going pulse then sets latch 1920, providing a high-level on the wakeup control signal. Latch 1920 may also be reset (e.g., when satellite 404 is entering the sleep mode).

Figure 20:
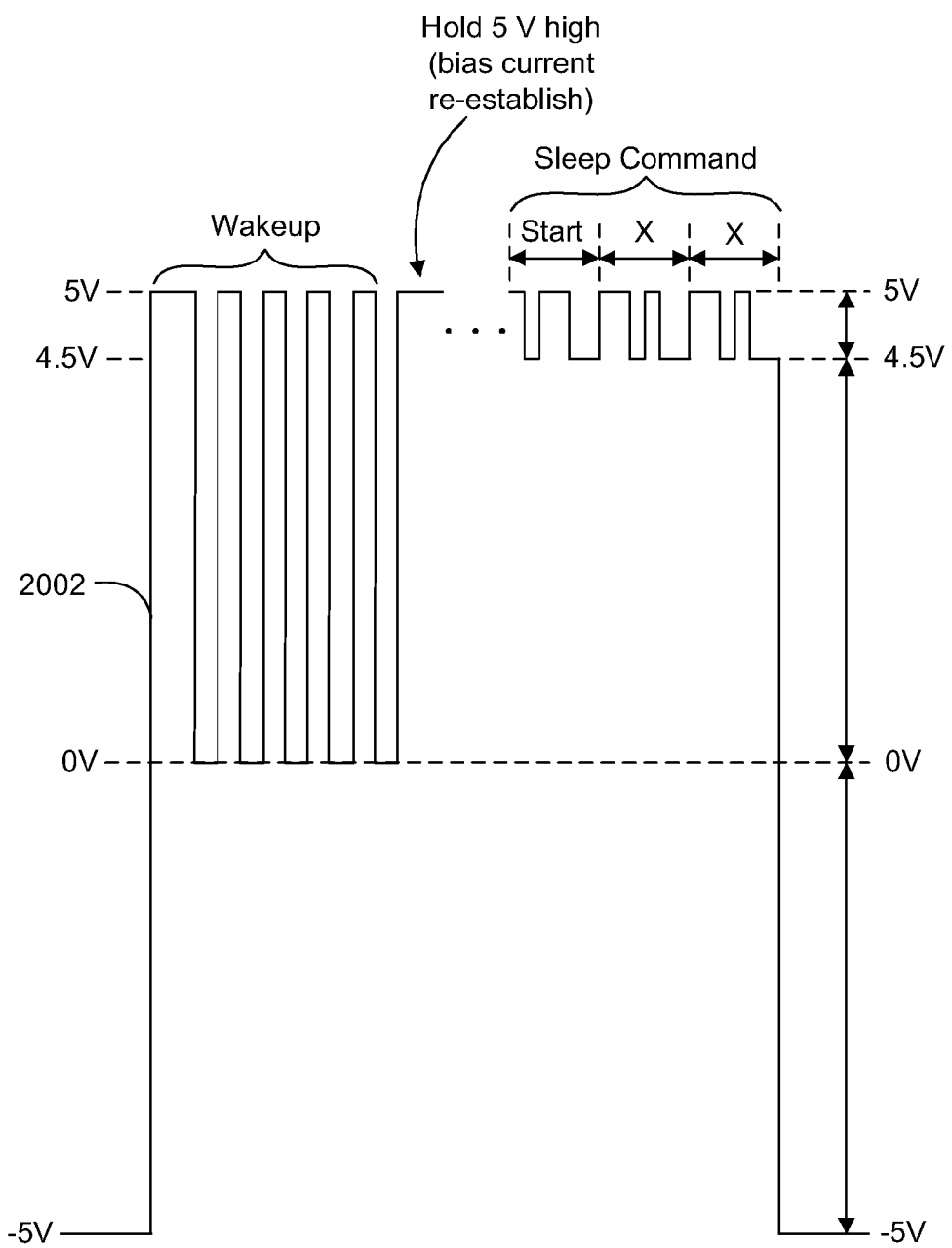
FIG. 20 depicts a command sequence waveform in accordance with various aspects of the invention.

FIG. 20 depicts a command sequence waveform 2002 for wakeup and sleep commands in accordance with various aspects of the invention. The leftmost pulse set "wakes" the IC, followed by a "power up" pulse. As shown, the wakeup command can include a series of pulses, such as five pulses, on a lead line, where the pulses range from about 0 V to about 5 V. Any other suitable voltage ranges can be used for the wakeup pulses, such as voltages having absolute values in a range of from about 1.5 V to about 8 V, including from about 3.3 V to about 6V, and more specifically about 5 V. For example, following the series of wakeup pulses and bias current re-establishment, may be commands to set switch configuration, verify the configuration, or put the device back to sleep (e.g., a Start command followed by sequential 'X' symbols). Separating each command may be a negative going pulse that mirrors the amplitude and duration for each command, such as by going to about negative 5 V. Following wakeup signal activation, a high level (e.g., about 5 V) may be held across lead lines $S_1$ and $S_2$ for about 5 uSec so that bias currents may be re-established, and internal supplies recharged, prior to communications signaling. For an initial chip power-up situation, this high level may last as long as about 25 uSec.

Communications signaling (e.g., from about 4.5 V to about 5 V) may include a series of commands for establishing lead configuration. In sending these commands, when a lead or satellite device is configured, charge is transferred between electrodes. A negative going pulse that immediately follow one or more commands, and may send an equal current going in the opposite direction, thus balancing the charge. Alternatively, balancing the charge (e.g., driving a lead line to about −5 V) can also occur between wakeup, the re-establish of bias currents or any suitable refresh or power up operation, and command. In any event, electrode charge balance is an important feature to ensure implantable electrode longevity.

As alternatives to wakeup detection or signaling being pulse or frequency dependent (e.g., a number of pulses), wakeup control can also be implemented as signal phase or signal amplitude dependent, or signal pulse width detection, or a combination of a signature inclusive of any combination of amplitude, frequency and/or pulse width. Further, a sleep mode entry can be determined by any suitable signature detection (e.g., no satellite device access for at least a predetermined time period), as opposed to being a direct command. For example, if there is no command received in a satellite device for some extended amount of time, the device can re-enter a sleep mode. For example, this extended amount of time can be any suitable time, such as a time in a range of from about 20 mSec to 500 mSec, including from about 50 mSec to 200 mSec, and more specifically about 100 mSec. The device can remain in this sleep mode until another wakeup command or signature is received. Once wakeup has been achieved, the device is equipped to receive other commands.

Research indicates that pulses having amplitudes of about 5 V may start to capture tissue with a duration of about 50 uSec. In designing command sequences, effort is made to minimize the duration and avoid cardiac tissue capture, which would not be desirable. However, that is not always possible, and one alternative to avoid tissue capture is to only issue commands during the heart's refractory period. That increases the time required to configure a lead, which may be undesirable. Another alternative, depicted here, uses bi-polar signaling. The negative going pulse which follows each command causes the ion channel to close, stopping tissue capture. Animal testing has verified this. In one test the "command" pulse duration was slowed to about 500 us with no tissue capture evidence.

Various aspects can also allow for area savings in the satellite IC implementation, as compared to other approaches. Utilizing only one signal line for communicating encoded data, as opposed to having two or more lines, such as for data, clock, and other signals, allows for area reduction based on fewer bond pads, and associated circuitry. Also, power savings in various aspects can be about 50%, or as high as about 70%, about 90%, and even as high as about 98% in some cases, when compared against a three-wire approach with full swing transitions, as opposed to one wire with small swing (e.g., about 500 mV) transitions, and at the same transmission frequency.

Satellite Detection with Interrogate

Various aspects include approaches for interrogation of satellite devices, such as the talkback approach discussed above. Some interrogations may be used to determine when a lead or satellite is not present or not responsive. In one interrogation approach, a value of 0xFF may be returned when a satellite 404 is not present or responsive. However, if 0xFF is a valid satellite configuration with all electrodes on and connected to the anode, ambiguous results may be received at controller 402. Changing the return value to 0x00 may also not be viable, as this may correspond to a valid result when all the electrodes are cleared.

Various aspects can detect lead or satellite 404 not being present or not responsive, and may involve a talkback receiver with digital logic to generate two bits of information: return data and an error bit.

Figure 21:
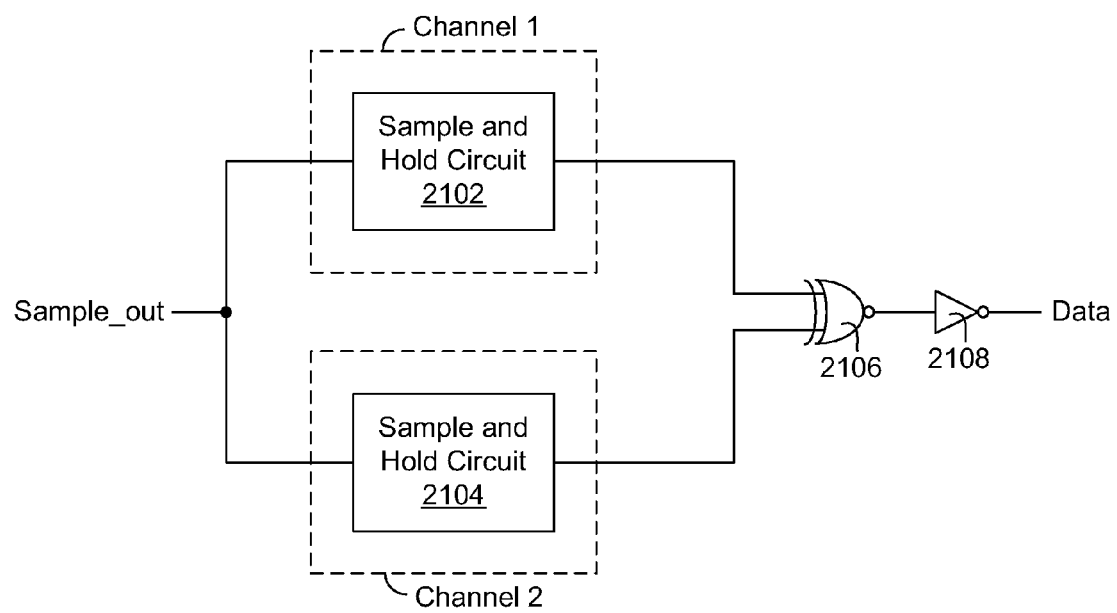
FIG. 21 depicts a satellite detection and interrogation circuit portion in accordance with various aspects of the invention.

FIG. 21 depicts a satellite detection and interrogation circuit portion in accordance with various aspects of the invention. Channel 1 includes sampling and hold circuit 2102 with comparison to return 0xFF for an unresponsive satellite. Channel 2 includes sample and hold circuit 2104, and can return a complimentary output of 0x00 for an unresponsive lead or satellite. For valid interrogation conditions, the output from channels 1 and 2 may be the same.

Performing an exclusive-OR (XOR) operation (e.g., using XNOR gate 2106 and inverter 2108) on the outputs of channels 1 and 2 (sample and hold circuits 2102 and 2104) can generate an error bit that may be latched when the error bit returns a high (logic '1') value. The error bit can be routed to either to a register for latching (e.g., a status or other register bit). Of course, any suitable logic or circuitry can also be used in various aspects.

As such, aspects of the invention include a multi-channel lead interrogator that determines when a lead in an in-body computing system fails by splitting a transmission signal into two or more channels and comparing said channels. The number of channels may vary, ranging from 1-6 channels, such as from 1-4 channels, including 2 channels. As a result, the multi channel lead interrogator allows for in-body computing systems to accurately determine when a component (e.g. lead, satellite, etc.) has failed, and allows for users to take appropriate action to remedy the failure.

The fault detection provided by the multi channel lead interrogator is important for in-body computing system operation. If an in-body computing system believes a component is functional when a component is actually not, the system may waste resources (e.g. power, current, etc.) on the malfunctioning component and produce unhelpful results.

Furthermore, sending resources to malfunctioning components may be harmful for the system. The malfunctioning component may receive too much current and drain resources from other parts of the system. Alternatively, the malfunctioning component not receive any current, and attempts by the system to provide current to the malfunctioning component may result in overheating other parts of the system.

A benefit of the multi channel lead interrogator is the ability to detect faults without a redundant transmission line. Redundant transmission lines require more space and power to implement, which may be tolerable in larger systems. However, in in-body computing environments, space and power are extremely scarce. It may not be practical or efficient to have multiple transmission lines running through the body. The multi channel lead interrogator avoids this problem by performing the fault analysis on the receiver end of a single transmission line.

The multi channel lead interrogator can also detect faults without using a parity bit. When used in error correction and fault detection systems, a parity bit's sole purpose is to flag an error or fault. However, the parity bit requires an extra bit of data to be carried on the transmission line and requires additional resources to compute. This may lead to slower calculations or larger computation circuits. The multi channel lead interrogator avoids the problems of a parity bit by performing fault analysis in stages.

An important aspect of the multi channel lead interrogator is that it has the ability to use hysteresis to distinguish when two signals are approximately equal. When comparing multiple signals, comparators often retain their previous output due to hysteresis if input signal dos not overcome hysteresis threshold. For example, if signals A is at 1, and is at 0, Hysteresis threshold is TH 0.5 the comparator will say A>B, provided A>B+TH. Now, if the input signal comes in intending to give A<B, the comparator output will retain the information from the previous signal until A<B−TH.

Using the hysteresis property in comparator multi channel lead interrogator can determine three states from an incoming signal. Bit 1 when A>B, Bit 0 if A<B, Error if A−B<TH. If signal A and B are time delayed signals, during the time when signal A has arrived but signal B has not, A<B. During that transient time between two signals comparator may switch in wrong state. The multi channel lead interrogator exploits hysteresis, and overcomes transient time issue by synchronizing the comparator values with a clock signal.

The transmission signal may originate from a component (e.g. lead, satellite, etc.) and may take a variety of forms. The transmission signal may be a discrete wave form, an analog wave form, or a square wave, among others. Furthermore, though the present invention was designed for use in single transmission line systems, the present invention may also be used as a complimentary fault detection function in systems with multiple transmission lines.

Figure 23:
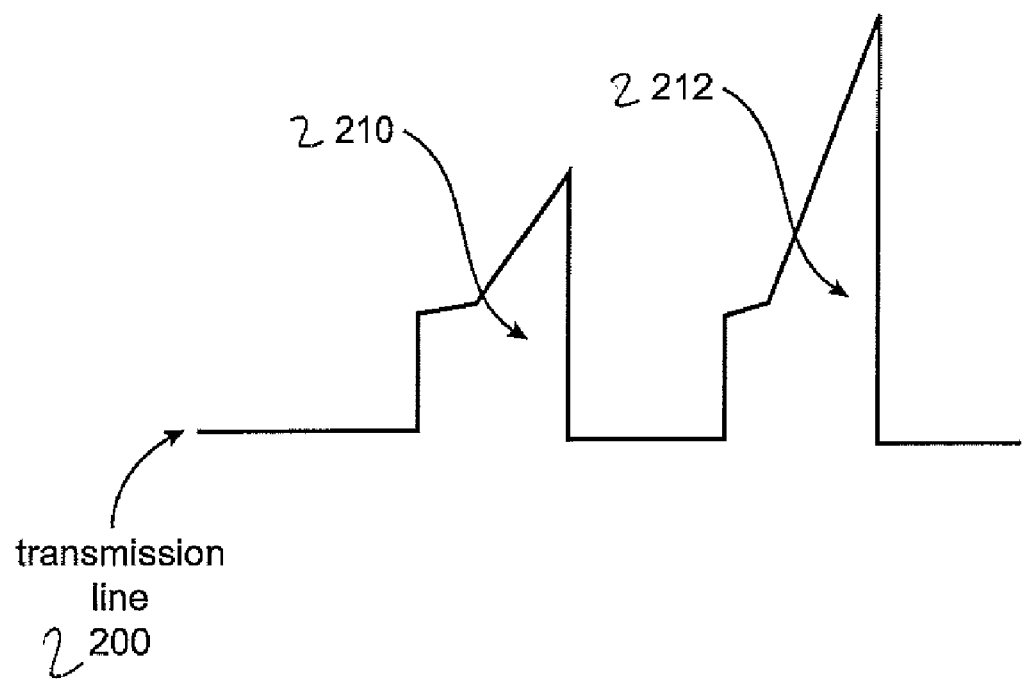
FIG. 23 illustrates one form of a transmission signal used in one embodiment of the current invention.

FIG. 23 illustrates one embodiment of a transmission signal used in the present invention. In FIG. 23, transmission signal 2200 has two different wave segments: segment 2210 and segment 2212. The number of wave segments may vary, ranging from about 1-5 segments, such as from about 2-4 segments, including about 2 segments. Each segment corresponds to a channel in the splitting circuit. For example, in FIG. 23, there are two segments. Therefore, there will be two channels in the splitting circuit.

Segment 2210 is characterized by a square wave, with a triangular peak. The peak of the voltage may vary, ranging from about 0.5V-5V, such as from about 2V-4V, including about 3V. Segment 2212 is characterized by a square wave, but with a taller triangular peak. The differences between the segments can take many forms. Instead of differing triangular peaks, they may be sinusoidal peaks, trapezoidal peaks, or entirely wave form (e.g. non-square wave), among others.

When a component (e.g. lead, satellite, etc.) is working, segment 2210 and 2212 should be different. If, and only if, segment 2210 and 2212 are the same will the multi channel lead interrogator detect a fault.

Figure 22:
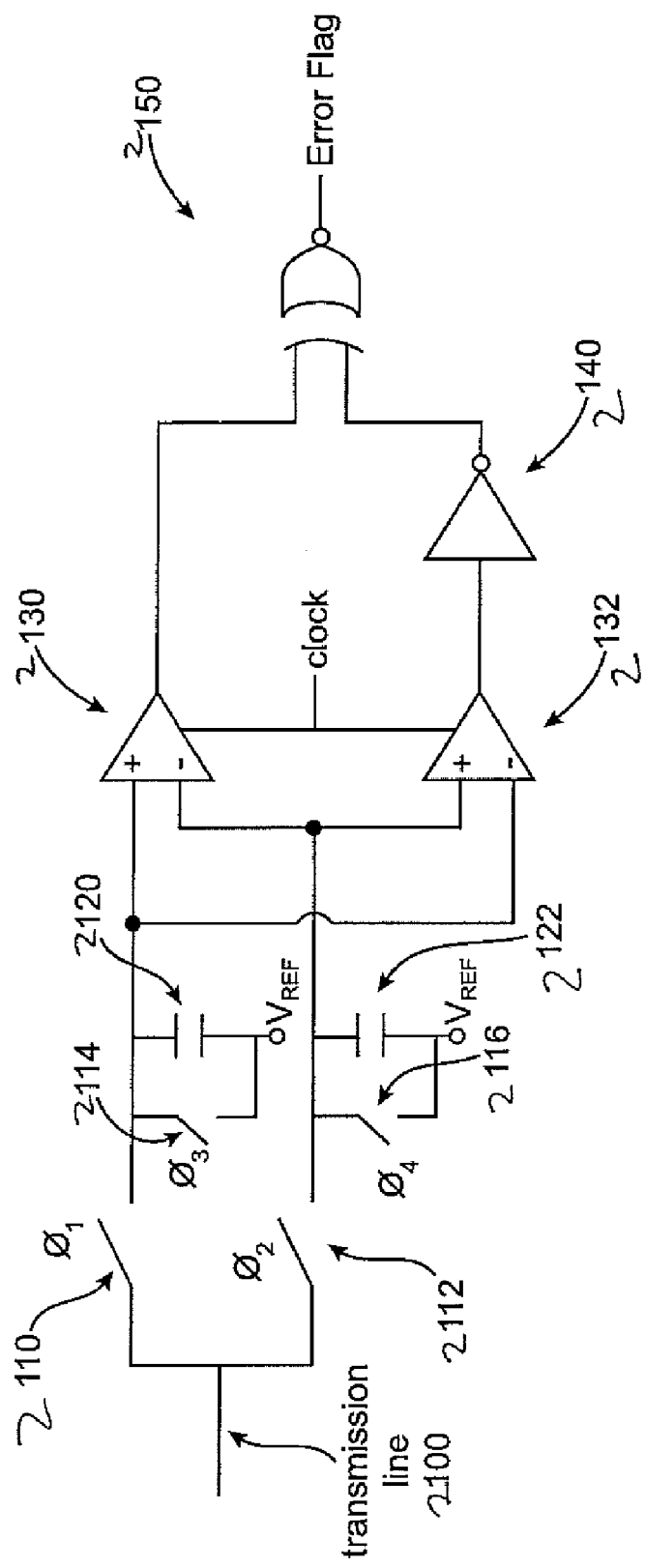
FIG. 22 illustrates a preferred schematic of switches, capacitors, comparators, invertors, and xor gates for one embodiment of the present invention.

FIG. 22 illustrates one embodiment of the present invention. In FIG. 22, transmission signal 2100 is split into two channels. Each channel has a switch, 2110 and 2112, respectively. Switches 2110 and 1212 close at times $\phi_1$ and $\phi_2$, respectively. Switches 2114 and 2116 initially are open, so when switches 2110 and 2112 closed, capacitors 2120 and 2122 charge according to the inputs of channel 2110 and 2112. The capacitor values may vary, ranging from about 200 fF-20 pF, such as from about 1 pF-10 pF, including about 5 pF. Switches 2114 and 2116 close at times $\phi_3$ and $\phi_4$, respectively, to discharge the capacitor 2120 and 2122. The voltages across the capacitors may vary, and range from about 0.5V-5V, such as from about 2V-4V, including about 3V. After capacitors 2120 and 2122 are fully charged, their voltages are compared by comparators 2130 and 2132. Comparators 2130 and 2132 are reset to same value output prior to comparison.

Comparator 2130 has capacitor 2120's value at its positive terminal and capacitor 2122's value at its negative terminal. Similarly, comparator 2132 has capacitor 2122's value at its positive terminal and capacitor 2120's value at its negative terminal. The output of comparator 2132 is then inverted by inverter 2140, and then XOR-ed with the output of comparator 2130 by XOR gate 2150.

In one embodiment of the current invention, the output of XOR gate 2150 will be 0 during a fault-less detection. Transmission signal 2100 comes into the splitting and comparator circuit, and has two segments. The two segments are different, so they charge capacitors 2120 and 2122 to different levels. Since comparators 2130 and 2132 have complimentary inputs, (e.g. capacitor 2120 positive in one, and capacitor 2120 negative in the other), the two comparators will output complimentary signals (e.g. one comparator outputs 1, the other comparator outputs 0.) If you XOR the complimentary signals, the result will always be a 1. However, inverter 2140 inverts the output of comparator 2132, so the output of inverter 2140 will always be the same as comparator 2130 (during a fault-less detection). Therefore, since the inputs of XOR gate 2150 are always match, the output of XOR gate 2150 will always be 0 for fault-less detection.

If during fault condition charge capacitors 2120 and 2122 are at same levels, the comparators 2130 and 2132 will retain their reset value due to hysteresis. That will make output of comparator 2130 and inverter 2140 complimentary. For similar reasons, in one embodiment of the present invention, XOR gate 2150 will output a 1 only if the two segments in transmission linen 2100 are equal, and therefore a fault has occurred.

The error bit output of XOR gate 2150 can be used in many ways. The error bit can be used to flag an error which would then be used in other sections of an in-body computing system, or can be stored in a remote storage device (e.g. computer, PDA, server, cell phone etc.), among others.

Figure 24:
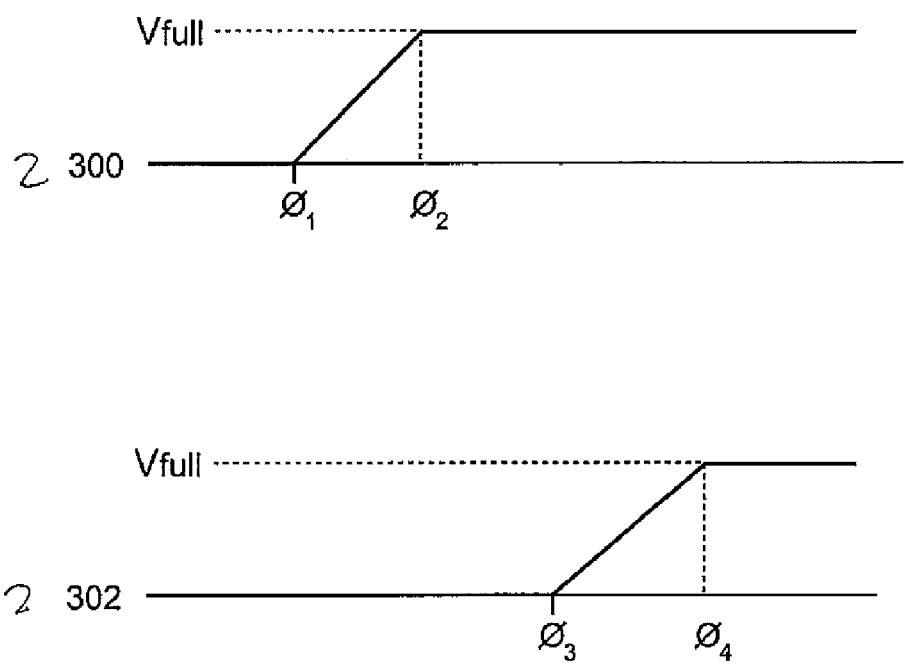
FIG. 24 illustrates hysteresis affecting the comparisons of two channels.

An aspect of certain embodiments of the invention is the synchronization of the comparators with a clock signal. This synchronization is designed to overcome the effects of signal transients. FIG. 24 illustrates the effects of hysteresis. In FIG. 24, the voltage stored in capacitors 2300 and 2302 are initially 0. At $\phi_1$, capacitor 2300 begins to charge. At $\phi_2$, capacitor 2300 is fully charged ($V_{full}$). At $\phi_3$, capacitor 2302 begins to charge, and continues to charge until $\phi_4$, when capacitor 2302 becomes fully charged ($V_{full}$). If a comparator was to continuously compare the charges across capacitor 2300 and 2302 during the time interval between $\phi_2$ and $\phi_3$, the comparator would detect that 2300>2302. Similarly, after $\phi_4$, the comparator would not be able to detect that 2300=2302 because of hysteresis. By synchronizing the comparators with a clock signal, and resetting to their "zero" settings at set intervals prior to comparison, allows for accurate comparisons.

Systems

Also provided are systems that include one more devices as described above, such as an implantable pulse generator. The systems of the invention may be viewed as systems for communicating information within the body of subject, e.g., human, where the systems include both a first implantable medical device, such as an IPG device described above, that includes a transceiver configured to transmit and/or receive a signal; and a second device comprising a transceiver configured to transmit and/or receive a signal. The second device may be a device that is inside the body, on a surface of the body or separate from the body during use.

Also provided are methods of using the systems of the invention. The methods of the invention generally include: providing a system of the invention, e.g., as described above, that includes first and second medical devices, one of which may be implantable; and transmitting a signal between the first and second devices. In various aspects, the transmitting step includes sending a signal from the first to said second device. In various aspects, the transmitting step includes sending a signal from the second device to said first device. The signal may be transmitted in any convenient frequency, where in various aspects the frequency ranges from about 400 to about 405 MHz. The nature of the signal may vary greatly, and may include one or more data obtained from the patient, data obtained from the implanted device on device function, control information for the implanted device, power, etc.

Use of the systems may include visualization of data obtained with the devices. Some of the present inventors have developed a variety of display and software tools to coordinate multiple sources of sensor information which will be gathered by use of the inventive systems. Examples of these can be seen in international PCT application serial no. PCT/US2006/012246; the disclosure of which application, as well as the priority applications thereof are incorporated in their entirety by reference herein.

Aspects of the systems and methods of use described above are reviewed in greater detail below.

Electrode Satellite Structures

Embodiments of the invention further include electrode assemblies, such as electrode satellite structures, where the structures include an integrated circuit control device, e.g., including a circuit as reviewed above, and at least one electrode element, where these embodiments includes a self-referencing communication system (or at least components thereof) of the invention, e.g., as described above. As such, embodiments of the satellite structures include control circuitry, e.g., in the form of an IC (e.g., an IC inside of the support), such that the satellite structure is addressable. In certain embodiments, the structure includes two or more electrode elements, such as three or more electrode elements, including four or more electrode elements, e.g., where the structure is a segmented electrode structure.

As reviewed above, the integrated circuit may be hermetically sealed or protected. Embodiments of hermetically sealed IC chips include, but are not limited to, those described in PCT application serial Nos. PCT/US2005/046815 and PCT/US2007/009270; the disclosures of hermetically sealed structures provided in these applications being specifically incorporated herein by reference.

As summarized above, aspects of the invention include implantable medical devices that include the electrode structures as described above. By implantable medical device is meant a device that is configured to be positioned on or in a living body, where in certain embodiments the implantable medical device is configured to be implanted in a living body. Embodiments of the implantable devices are configured to maintain functionality when present in a physiological environment, including a high salt, high humidity environment found inside of a body, for 2 or more days, such as about 1 week or longer, about 4 weeks or longer, about 6 months or longer, about 1 year or longer, e.g., about 5 years or longer. In certain embodiments, the implantable devices are configured to maintain functionality when implanted at a physiological site for a period ranging from about 1 to about 80 years or longer, such as from about 5 to about 70 years or longer, and including for a period ranging from about 10 to about 50 years or longer. The dimensions of the implantable medical devices of the invention may vary. However, because the implantable medical devices are implantable, the dimensions of certain embodiments of the devices are not so big such that the device cannot be positioned in an adult human.

Vascular Leads

Embodiments of the invention also include medical carriers that include one or more electrode satellite structures, e.g., as described above. Carriers of interest include, but are not limited to, vascular lead structures, where such structures are generally dimensioned to be implantable and are fabricated from a physiologically compatible material. With respect to vascular leads, a variety of different vascular lead configurations may be employed, where the vascular lead in certain embodiments is an elongated tubular, e.g., cylindrical, structure having a proximal and distal end. The proximal end may include a connector element, e.g., an IS-1 connector, for connecting to a control unit, e.g., present in a "can" or analogous device. The lead may include one or more lumens, e.g., for use with a guidewire, for housing one or more conductive elements, e.g., wires, etc. The distal end may include a variety of different features as desired, e.g., a securing means, etc.

In certain embodiments of the subject systems, one or more sets of electrode satellites as described above are electrically coupled to at least one elongated conductive member, e.g., an elongated conductive member present in a lead, such as a cardiovascular lead. In certain embodiments, the elongated conductive member is part of a multiplex lead. Multiplex lead structures may include 2 or more satellites, such as 3 or more, 4 or more, 5 or more, 10 or more, 15 or more, 20 or more, etc. as desired, where in certain embodiments multiplex leads have a fewer number of conductive members than satellites. In certain embodiments, the multiplex leads include 3 or less wires, such as only 2 wires or only 1 wire. Multiplex lead structures of interest include those described in application Ser. No. 10/734,490; PCT/US2005/031559; PCT/US2005/46815; and Ser. No. 11/734,617; the disclosures of the various multiplex lead structures of these applications being herein incorporated by reference. In some embodiments of the invention, the devices and systems may include onboard logic circuitry or a processor, e.g., present in a central control unit, such as a pacemaker can. In these embodiments, the central control unit may be electrically coupled to the lead by a connector, such as a proximal end IS-1 connection.

FIG. 2 illustrates an external view of a number of exemplary pacing satellites, in accordance with a multiplex lead embodiment of the present invention. According to one embodiment, a pacing lead 200 (e.g., right ventricular lead 102 or left ventricular lead 105 of FIG. 1) accommodates two bus wires S1 and S2, which are coupled to a number (e.g., eight) of satellites, such as satellite 202. FIG. 2 also shows satellite 202 with an enlarged view. Satellite 202 includes electrodes 212, 214, 216, and 218, located in the four quadrants of the cylindrical outer walls of satellite 202 and supported by a support structure of the invention. Each satellite also contains a control chip inside the structure which communicates with a pacing and signal-detection system to receive configuration signals that determine which of the four electrodes are to be coupled to bus wires S1 or S2.

The configuration signals, the subsequent pacing pulse signals, and the analog signals collected by the electrodes can all be communicated through bus wires S1 and S2, in either direction. Although shown in a symmetrical arrangement, electrodes 212, 214, 216 and 218 may be offset along lead 200 to minimize capacitive coupling among these electrodes. The quadrant arrangement of electrodes allows administering pacing current via electrodes oriented at a preferred direction, for example, away from nerves, or facing an electrode configured to sink the pacing current. Such precise pacing allows low-power pacing and minimal tissue damage caused by the pacing signal.

The leads may further include a variety of different effector elements, which elements may employ the satellites or structures distinct from the satellites. The effectors may be intended for collecting data, such as but not limited to pressure data, volume data, dimension data, temperature data, oxygen or carbon dioxide concentration data, hematocrit data, electrical conductivity data, electrical potential data, pH data, chemical data, blood flow rate data, thermal conductivity data, optical property data, cross-sectional area data, viscosity data, radiation data and the like. As such, the effectors may be sensors, e.g., temperature sensors, accelerometers, ultrasound transmitters or receivers, voltage sensors, potential sensors, current sensors, etc. Alternatively, the effectors may be intended for actuation or intervention, such as providing an electrical current or voltage, setting an electrical potential, heating a substance or area, inducing a pressure change, releasing or capturing a material or substance, emitting light, emitting sonic or ultrasound energy, emitting radiation and the like.

Effectors of interest include, but are not limited to, those effectors described in the following applications by at least some of the inventors of the present application: U.S. patent application Ser. No. 10/734,490; U.S. patent application Ser. No. 11/219,305; International Application No. PCT/US2005/046815; U.S. patent application Ser. No. 11/324,196; U.S. patent application Ser. No. 10/764,429; U.S. patent application Ser. No. 10/764,127; U.S. patent application Ser. No. 10/764,125; International Application No. PCT/US2005/

046815; U.S. application Ser. No. 11/368,259; International Application No. PCT/US2004/041430; U.S. patent application Ser. No. 11/249,152; and International Application Serial No. PCT/USUS05/39535. These applications are incorporated in their entirety by reference herein.

Implantable Pulse Generators

Embodiments of the invention further include implantable pulse generators. Implantable pulse generators may include: a housing which includes a power source and an electrical stimulus control element; one or more vascular leads as described above, e.g., 2 or more vascular leads, where each lead is coupled to the control element in the housing via a suitable connector, e.g., an IS-1 connector. In certain embodiments, the implantable pulse generators are ones that are employed for cardiovascular applications, e.g., pacing applications, cardiac resynchronization therapy applications, etc. As such, in certain embodiments the control element is configured to operate the pulse generator in a manner so that it operates as a pacemaker, e.g., by having an appropriate control algorithm recorded onto a computer readable medium of a processor of the control element. In certain embodiments the control element is configured to operate the pulse generator in a manner so that it operates as a cardiac resynchronization therapy device, e.g., by having an appropriate control algorithm recorded onto a computer readable medium of a processor of the control element.

An implantable pulse generator according to an embodiment of the invention is depicted in FIG. 1. FIG. 1 illustrates the locations of a number of pacing satellites incorporated in multi-electrode pacing leads, in accordance with an embodiment of the present invention. A pacing and signal detection system 101 provides extra-cardiac communication and control elements for the overall system. In some embodiments, pacing and signal detection system 101 may be, for example, a pacing can of a pacemaker residing in an external or extra-corporeal location.

Right ventricular lead 102 emerges from pacing and signal detection system 101 and travels from a subcutaneous location from pacing and signal detection system 101 into the patient's body (e.g., preferably, a subclavian venous access), and through the superior vena cava into the right atrium. From the right atrium, right ventricle lead 102 is threaded through the tricuspid valve to a location along the walls of the right ventricle. The distal portion of right ventricular lead 102 is preferably located along the intra-ventricular septum, terminating with a fixation in the right ventricular apex. Right ventricular lead 102 includes satellites positioned at locations 103 and 104. The number of satellites in ventricular lead 102 is not limited, and may be more or less than the number of satellites shown in FIG. 1.

Similarly, left ventricular lead 105 emerges from pacing and signal detection system 101, following substantially the same route as right ventricular lead 102 (e.g., through the subclavian venous access and the superior vena cava into the right atrium). In the right atrium, left ventricular lead 105 is threaded through the coronary sinus around the posterior wall of the heart in a cardiac vein draining into the coronary sinus. Left ventricular lead 105 is provided laterally along the walls of the left ventricle, which is likely to be an advantageous position for bi-ventricular pacing. FIG. 1 shows satellites positioned at locations 106 and 107 along left ventricular lead 105.

Right ventricular lead 102 may optionally be provided with pressure sensor 108 in the right ventricle. A signal multiplexing arrangement allows a lead to include such active devices (e.g., pressure sensor 108) for pacing and signal collection purposes (e.g., right ventricular lead 102). Pacing and signal detection system 101 communicates with each of the satellites at locations 103, 104, 106 and 107. The electrodes controlled by the satellites may also be used to detect cardiac depolarization signals. Additionally, other types of sensors, such as an accelerometer, strain gauge, angle gauge, temperature sensor, can be included in any of the leads.

In the above system, the device components can be connected by a multiplex system (e.g., as described in published U.S. patent application publication Ser. No. 10/734,490; PCT/US2005/031559; PCT/US2005/46815; and Ser. No. 11/734,617; the disclosures of which are herein incorporated by reference), to the proximal end of electrode lead 105. The proximal end of electrode lead 105 connects to a pacemaker 101, e.g., via an IS-1 connector.

During certain embodiments of use, the electrode lead 105 is placed in the heart using standard cardiac lead placement devices which include introducers, guide catheters, guidewires, and/or stylets. Briefly, an introducer is placed into the clavicle vein. A guide catheter is placed through the introducer and used to locate the coronary sinus in the right atrium. A guidewire is then used to locate a left ventricle cardiac vein. The electrode lead 105 is slid over the guidewire into the left ventricle cardiac vein and tested until an optimal location for CRT is found. Once implanted a multi-electrode lead 105 still allows for continuous readjustments of the optimal electrode location.

The electrode lead 102 is placed in the right ventricle of the heart. In this view, the electrode lead 102 is provided with one or multiple electrodes 103,104.

Electrode lead 102 is placed in the heart in a procedure similar to the typical placement procedures for cardiac right ventricle leads. Electrode lead 102 is placed in the heart using the standard cardiac lead devices which include introducers, guide catheters, guidewires, and/or stylets. Electrode lead 102 is inserted into the clavicle vein, through the superior vena cava, through the right atrium and down into the right ventricle. Electrode lead 102 is positioned under fluoroscopy into the location the clinician has determined is clinically optimal and logistically practical for fixating the electrode lead 102.

Summarizing aspects of the above description, in using the implantable pulse generators of the invention, such methods include implanting an implantable pulse generator e.g., as described above, into a subject; and the implanted pulse generator, e.g., to pace the heart of the subject, to perform cardiac resynchronization therapy in the subject, etc. The description of the present invention is provided herein in certain instances with reference to a subject or patient. As used herein, the terms "subject" and "patient" refer to a living entity such as an animal. In certain embodiments, the animals are "mammals" or "mammalian," where these terms are used broadly to describe organisms which are within the class mammalia, including the orders carnivore (e.g., dogs and cats), rodentia (e.g., mice, guinea pigs, and rats), lagomorpha (e.g. rabbits) and primates (e.g., humans, chimpanzees, and monkeys). In certain embodiments, the subjects, e.g., patients, are humans.

During operation, use of the implantable pulse generator may include activating at least one of the electrodes of the pulse generator to deliver electrical energy to the subject, where the activation may be selective, such as where the method includes first determining which of the electrodes of the pulse generator to activate and then activating the electrode. Methods of using an IPG, e.g., for pacing and CRT, are disclosed in Application Serial Nos.: PCT/US2005/036035; PCT/US2005/031559; PCT/US2005/46811; PCT/US2005/46815; and Ser. No. 11/734,617; the disclosures of the various methods of operation of these applications being herein incorporated by reference and applicable for use of the present devices.

Methods of Making

The subject circuits, structures and devices described herein may be fabricated using any convenient protocol.

Aspects of the invention include methods of making a vascular lead electrode satellite, where the method includes providing an electrode support as described above and positioning an electrode element in a recess of the support, and in various aspects additionally includes placing an IC (such as the integrated circuits reviewed above) in the support such that the IC is electrically coupled to the electrode element(s) in the recess(es) of the support. In various aspects, the positioning step includes fitting a premade electrode element into the recess, e.g., by sliding the electrode into the recess. As such, a premade electrode element, such as a petal electrode as described in PCT/US2005/46811 titled "Implantable Addressable Segmented Electrodes" filed on Dec. 22, 2005, may be slid into the recess to produce the desired electrode structure. In various aspects, the methods include producing electrodes in recesses of the support, e.g., via a deposition protocol, such as cathodic arc deposition. Further descriptions of methods of producing electrode assemblies are provided in provisional application Ser. No. 60/865,760 filed on Nov. 14, 2006, the disclosure of which is herein incorporated by reference.

Kits

Also provided are kits that include the circuits and/or implantable medical devices and systems or components thereof, e.g., that include the subject circuits, e.g., as reviewed above. In various aspects, the kits further include at least a control unit, e.g., in the form of a pacemaker can.

In various aspects of the subject kits, the kits will further include instructions for using the subject devices or elements for obtaining the same (e.g., a website URL directing the user to a webpage which provides the instructions), where these instructions are typically printed on a substrate, which substrate may be one or more of: a package insert, the packaging, reagent containers and the like. In the subject kits, the one or more components are present in the same or different containers, as may be convenient or desirable.

It is to be understood that this invention is not limited to particular embodiments, or various aspects described, as such may vary. It is also to be understood that the terminology used herein is for the purpose of describing particular embodiments or various aspects only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of various aspects described and illustrated herein has discrete components and features which may be readily separated from or combined with the features of any of the other several embodiments without departing from the scope or spirit of the present invention. Any recited method can be carried out in the order of events recited or in any other order which is logically possible.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments and various aspects that are shown and described herein. Rather, the scope and spirit of present invention is embodied by the appended claims.

What is claimed is:

1. An implantable integrated circuit, comprising:
   (a) a first capacitor configured to be charged when a first phase control signal is asserted, said first phase control signal being related to a first predetermined phase of an encoded signal;
   (b) a second capacitor configured to be charged when a second phase control signal is asserted, said second phase control signal being related to a second predetermined phase of said encoded signal; and
   (c) a first comparator coupled to said first and second capacitors, said first comparator being configured to provide a first comparison result that indicates which of said first and second predetermined phases has a longer duration.

2. The implantable integrated circuit of claim 1, further comprising a second comparator configured to provide a second comparison result that indicates which of a third and a fourth predetermined phase of said encoded signal has a longer duration.

3. The implantable integrated circuit of claim 2, further comprising digital logic configured to receive said first and second comparison results and to determine a match to a symbol therefrom.

4. The implantable integrated circuit of claim 1, wherein said first and second phases are about 5 V, and said third and fourth phases are about 4.5 V.

5. The implantable integrated circuit of claim 1, wherein said encoded signal comprises a single wire interface to a controller.

6. A method for clock and data recovery in an implantable device, the method comprising:
   (a) recovering a first clock from first and second high phases of an encoded signal, and a second clock from first and second low phases of said encoded signal;
   (b) deriving first, second, third, and fourth phase control signals from said first and second recovered clocks;
   (c) comparing pulse durations of said first and second phase control signal to generate a first comparison result, and comparing pulse durations of said third and fourth phase control signals to generate a second comparison result; and
   (d) determining one of four symbols corresponding to said encoded signal using said first and second comparison results.

7. The method of claim 6, wherein said recovering said first and second clocks comprises translating said encoded signal into a full-swing signal.

8. The method of claim 6, wherein said comparing said pulse durations comprises charging capacitors for a time period corresponding to said phase control signal durations.

9. The method of claim 6, wherein said determining said one of four symbols comprises using digital logic that receives said first and second comparison results.

10. The method of claim 6, further comprising receiving said encoded signal from a controller on a single wire interface.

11. The method of claim 6, further comprising receiving a wakeup indication to enable said recovering.

12. A computer-readable storage device, comprising:
   (a) one or more instructions for recovering a first clock from first and second high phases of an encoded signal, and a second clock from first and second low phases of said encoded signal;
   (b) one or more instructions for deriving first, second, third, and fourth phase control signals from said first and second recovered clocks;
   (c) one or more instructions for comparing pulse durations of said first and second phase control signal to generate a first comparison result, and comparing pulse durations of said third and fourth phase control signals to generate a second comparison result; and
   (d) one or more instructions for determining one of four symbols corresponding to said encoded signal using said first and second comparison results.

13. The computer-readable storage device of claim 12, wherein said recovering said first and second clocks comprises one or more instructions for translating said encoded signal into a full-swing signal.

14. The computer-readable storage device of claim 12, wherein said comparing said pulse durations comprises one or more instructions for charging capacitors for a time period corresponding to said phase control signal durations.

15. The computer-readable storage device of claim 12, wherein said determining said one of four symbols comprises one or more instructions for using digital logic that receives said first and second comparison results.

16. The computer-readable storage device of claim 12, further comprising one or more instructions for receiving said encoded signal from a controller on a single wire interface.

17. The computer-readable storage device of claim 12, further comprising one or more instructions for receiving a wakeup indication to enable said recovering.

18. An implantable controller having an interface configured to communicate to an implantable satellite device, said interface comprising:
   (a) a ground terminal; and
   (b) a signal terminal configured to transmit an encoded signal to said implantable satellite device, wherein said encoded signal comprises first and second high phases and first and second low phases.

19. The implantable controller of claim 18, wherein said encoded signal comprises said first high phase, followed by said first low phase, followed by said second high phase, followed by said second low phase.

20. The implantable controller of claim 18, wherein said encoded signal comprises one of four symbols.

21. The implantable controller of claim 18, wherein said encoded signal comprises about a 500 mV variation over a nominal 5 V signal.

22. The implantable controller of claim 18, wherein said ground terminal is configured to be coupled to a human body.

\* \* \* \* \*